(12) United States Patent
Roper et al.

(10) Patent No.: US 11,286,458 B2
(45) Date of Patent: Mar. 29, 2022

(54) METHODS AND COMPOSITIONS FOR THE BIOLOGICAL CONTROL OF PLANT PATHOGENS

(71) Applicant: Commonwealth Scientific and Industrial Research Organisation, Acton (AU)

(72) Inventors: Margaret Roper, Acton (AU); Louise Thatcher, Acton (AU); Cathryn O'Sullivan, Acton (AU); Jonathan Anderson, Acton (AU); Cindy Myers, Acton (AU)

(73) Assignee: Commonwealth Scientific and Industrial Research Organisation, Acton (AU)

( * ) Notice: Subject to any disclaimer, the term of this patent is extended or adjusted under 35 U.S.C. 154(b) by 0 days.

(21) Appl. No.: 16/645,376

(22) PCT Filed: Sep. 11, 2018

(86) PCT No.: PCT/AU2018/050982
§ 371 (c)(1),
(2) Date: Mar. 6, 2020

(87) PCT Pub. No.: WO2019/046909
PCT Pub. Date: Mar. 14, 2019

(65) Prior Publication Data
US 2020/0296973 A1    Sep. 24, 2020

(30) Foreign Application Priority Data

Sep. 11, 2017 (AU) .................................. 2017903676
Jul. 31, 2018 (AU) .................................. 2018902770

(51) Int. Cl.
| | |
|---|---|
| *C12N 1/20* | (2006.01) |
| *A01N 63/28* | (2020.01) |
| *C12P 1/06* | (2006.01) |
| *C12N 3/00* | (2006.01) |
| *C12R 1/465* | (2006.01) |

(52) U.S. Cl.
CPC ............. *C12N 1/205* (2021.05); *A01N 63/28* (2020.01); *C12N 1/20* (2013.01); *C12N 3/00* (2013.01); *C12P 1/06* (2013.01); *C12R 2001/465* (2021.05)

(58) Field of Classification Search
None
See application file for complete search history.

(56) References Cited

U.S. PATENT DOCUMENTS 5,968,503 A     10/1999   Crawford
8,603,799 B2 *  12/2013   Martin, Jr .............. A01N 63/50
                                                      435/253.5

FOREIGN PATENT DOCUMENTS

WO      WO 01/52655 A2     7/2001

OTHER PUBLICATIONS

Roper, Margaret et al. Suppression of Fusarium Crown Rot in Wheat by Endophytic Actinobacteria Agriculture, Sep. 14, 2015, https://www.appsnet.org/Publications/Fremantle_Presentations/roper_margaret.pdf.
Shen, Ting et al., "Identification, solid-state fermentation and biocontrol effects of Streptomyces hygroscopicus B04 on strawberry root rot" Applied Soil Ecology, 2016, pp. 36-43, vol. 103.
International Search Report for PCT/AU2018/050982 dated Oct. 2, 2018.

* cited by examiner

*Primary Examiner* — Vera Afremova
(74) *Attorney, Agent, or Firm* — Knobbe Martens Olson & Bear LLP

(57) ABSTRACT

Provided herein are *Streptomyces* isolates, designated MH71 and MH243, cultures thereof, and compositions comprising the same. Also provided are uses of the isolates, cultures and compositions, for example, for treating and preventing infections and diseases caused by or associated with plant pathogen infections, reducing the susceptibility of plants to diseases caused by or associated with plant pathogen infections, and for inhibiting or reducing the growth of pathogens on plants.

8 Claims, 15 Drawing Sheets

A

B

| Actinobacteria Isolate | Suppression zone (mm) | | |
|---|---|---|---|
| | CS5642 | CS5834 | CS3427 |
| MH243 | 32 | 44 | 18 |
| MH71 | 25 | 27 | 35 |
| MH191 | 12 | 4 | 15 |
| MH192 | 11 | 18 | 18 |
| MH60 | 9 | 3 | 4 |
| MH51 | 8 | 15 | 13 |
| 8a | 7 | 2 | 4 |
| MH133 | 7 | 6 | 2 |

METHODS AND COMPOSITIONS FOR THE BIOLOGICAL CONTROL OF PLANT PATHOGENS

CROSS REFERENCE TO RELATED APPLICATIONS

This application is a U.S. National Phase Application of PCT International Application Number PCT/AU2018/050982, filed on Sep. 11, 2018, designating the United States of America and published in the English language, which is an International Application of and claims the benefit of priority to Australian Patent Application No. 2017903676, filed on Sep. 11, 2017, and Australian Patent Application No. 2018902770, filed on Jul. 31, 2018. The disclosures of the above-referenced applications are hereby expressly incorporated by reference in their entireties.

FIELD OF THE ART

The present disclosure relates generally to novel *Actinobacteria* and compositions containing same. Methods for the biological control of plant pathogens are also provided.

BACKGROUND

Plant disease as a result of pathogen infection represents a significant economic cost to modern agriculture. Current systems of agriculture often require one or a few crops or plant types to be grown over a large area. Such an ecologically unbalanced system is susceptible to disease. Plant fungal pathogens alone are responsible for losses in the order of billions of dollars globally to agricultural production. For example, soil/stubble-borne fungi cause diseases of wheat and canola that alone cost the Australian grain and oilseed industries >$250M annually (Murray G M & Brennan J P. (2009), 'The current and potential costs of diseases of wheat in Australia'. Grains Research and Development Corporation, Barton, ACT, Australia; Murray G M & Brennan J P. (2012), 'The current and potential costs from diseases of oilseed crops in Australia'. Grains Research and Development Corporation, Barton, ACT, Australia). The incidence of some of these diseases is on the rise, including *Fusarium* crown rot of wheat and *Sclerotinia* Stem Rot of canola.

*Sclerotinia* is one of the most devastating plant pathogens, causing stem rot disease on over 500 plant species and an increasing constraint to canola production. A global problem, *Sclerotinia* cost the world's largest canola producer (Canada) an estimated US$600 million in just one year (2010), and between 2005 and 2009 cost Australia AU$10.1 million per annum. Since 2009 canola production in Australia has doubled and along with it so has the cost of *Sclerotinia* stem rot, costing Western Australia alone an estimated $59 million in losses in 2013. The disease is notoriously difficult to control due to a number of confounding factors, for example, all commercial cultivars of canola are susceptible, the pathogen has a broad host range, its spores spread rapidly through air, its 'dormant' stage remains in soil for years and increased canola production in Australia has led to a build-up of pathogen load. The fungal pathogen responsible for *Rhizoctonia* root and hypocotyl rots of canola also has a high potential for disease severity in Australia. These diseases are predicted to result in annual losses of $29.4 million if not controlled (Murray G M & Brennan J P. (2012). 'The current and potential costs from diseases of oilseed crops in Australia'. Grains Research and Development Corporation, Barton, ACT, Australia).

*Fusarium graminearum*, a member of the fungal phylum Ascomycota is a plant pathogen which causes *fusarium* head blight. This is a devastating disease on wheat and barley. The pathogen is responsible for billions of dollars in economic losses worldwide each year. Infection causes shifts in the amino acid composition of wheat, resulting in shrivelled kernels and contaminating the remaining grain with mycotoxins, mainly deoxynivalenol, which inhibits protein biosynthesis; and zearalenone, an estrogenic mycotoxin. These toxins cause vomiting, liver damage, and reproductive defects in livestock, and are harmful to humans through contaminated food. Also a member of Ascomycota is *Fusarium pseudograminearum* which causes crown rot of wheat. Crown rot of wheat is an important plant disease that without management can have serious detrimental effects on entire fields of wheat causing white heads which have no grains, leading to large yield losses. The disease expression of *F. pseudograminearum* can develop during stressful water deficits in fields.

Bacterial plant pathogens pose similar problems in agriculture. For example *Xanthomonas ozyrae*, which causes bacterial blight, is one of the most important pathogens of rice, causing yield losses up to 50%. Similarly, *Pseudomonas syringae* is the causative agent of bacterial blight on a wide range of plant hosts including important broadacre and horticultural crops such as barley, tomato, *brassica* vegetables and fruit trees. Yield losses are compounded by the limited availability of control strategies and growing pesticide resistance.

Crop yield losses caused by fungal and bacterial pathogens are compounded by the limited availability of effective control strategies and growing pesticide resistance. Plant breeding programs have had some success in producing more tolerant varieties to some diseases but none of these show effective disease resistance across multiple pathogens. In some cases, despite great efforts to find resistance genes, for example against the devastating pathogen *F. pseudograrninearum*, no completely resistant variety is currently available. Furthermore many pathogens can persist by surviving or growing in the soil, stubble or on the roots of summer weeds, and act as a source of infection in the following crop.

Traditionally, control of plant pathogens such as fungi and bacteria has been pursued through the use of chemical fungicides, bactericides or pesticides. Such agents used as seed dressings and foliar sprays provide variable protection depending on the pathogen and timing of application (sprays). However, consumers are becoming increasingly concerned about chemical residues on plants and their effects on the environment. Moreover, although currently available chemicals can reduce disease incidence, timing of application is critical and difficult to achieve. Routine prophylactic application is uneconomical and undesirable. Furthermore, pathogens are becoming increasingly resistant to available chemicals.

The intractable nature of many fungal and bacterial diseases, their increasing and/or sporadic incidence, costly and challenging management with chemicals and their associated residues, dictates that there is a need to develop alternative environmentally sound control measures for the prevention and treatment of pathogenic diseases in plants.

Biological control (biocontrol) of plant pathogens is becoming an increasingly essential component in plant disease management. Many microorganisms are known to control various plant pathogens using multiple modes of activity, thereby reducing the risk of developing resistant pest populations. A wide range of biological control agents including bacteria, yeast and fungi have been investigated for use in controlling plant disease. Currently, there are a number of microbial-based biocontrol products commercially available, including products containing *Trichoderma* spp., *Bacillus* spp., and *Streptomyces* spp.

While potential biocontrol agents with antagonistic characteristics can be found, they must be carefully screened for a range of traits relevant to their proposed use. These traits include plant pathogenicity, antagonistic activity and specificity, amenability to manipulation in delivery systems and formulations, and performance under fluctuating field conditions with target plants. Establishment and performance in the field is often the most difficult challenge to overcome. Any biocontrol agent must be able to successfully establish and compete with the multitude of existing field microorganisms, in a way which is not harmful to target plants. Moreover, there are currently limited commercial biocontrol products on the market in Australia for most plant pathogens and diseases, including *Fusarium* crown rot, *Sclerotinia* and bacterial blight. Accordingly, there is a need for new biocontrol agents of plant pathogens which reduce the use of synthetic pesticides, fungicides and bactericides, and their residues, within the environment and which deliver a non-genetically modified approach to controlling pathogenic disease.

SUMMARY OF THE DISCLOSURE

A first aspect of the present disclosure provides *Streptomyces* strain MH71 deposited with the National Measurement Institute (NMI), Australia on 21 Feb. 2017 under Accession Number V17/004100.

A second aspect of the present disclosure provides *Streptomyces* strain MH243 deposited with the National Measurement Institute (NMI), Australia on 21 Feb. 2017 under Accession Number V17/004101.

In one embodiment the *Streptomyces* strains disclosed herein are isolated. In another embodiment, the strains are provided in the form of a culture, including a pure or substantially pure culture.

The *Streptomyces* strains MH71 and MH243 are capable of reducing or inhibiting the growth of pathogenic organisms which cause plant disease.

Accordingly, in a particular embodiment, *Streptomyces* selected from MH71 and MH243 are incorporated into a composition for treating or preventing a disease caused by, or associated with a plant pathogen, or for reducing the susceptibility of a plant to a disease caused by or associated with a plant pathogen.

In an embodiment, the composition comprises the culture combined with an agriculturally acceptable carrier, diluent or adjuvant which serves as a support medium for the *Streptomyces* and/or enhances the delivery of the microorganism to a plant. In an embodiment the composition comprises other additives which depend on the species of plant being treated, the identity and number of pathogens infecting the plant, the nature of the composition to be administered, the form in which the composition is to be administered, and the severity of infection or disease at the time of administration.

Accordingly, a third aspect of the present disclosure provides a composition comprising a culture of *Streptomyces* MH71 and/or MH243 and an agriculturally acceptable carrier, diluent or adjuvant.

In an embodiment, the *Streptomyces* used in the compositions are reproductively viable. In an exemplary embodiment, the *Streptomyces* are present in the composition in the form of reproductively viable spores or as hyphae e.g. spore-bearing mycelium.

Accordingly, in a fourth aspect the present disclosure provides a composition comprising in a reproductively viable form and amount, at least one isolate of *Streptomyces* selected from:
  (a) *Streptomyces* MH71 with the deposit number V17/004100; and
  (b) *Streptomyces* MH243 with the deposit number V17/004101; and
  an agriculturally acceptable carrier, diluent or adjuvant.

In accordance with the above aspects, in an embodiment, the composition comprises both isolated strains (a) and (b).

A fifth aspect of the present disclosure provides a composition produced by:
  (a) growing a culture of *Streptomyces* MH71 or MH243;
  (b) harvesting spores, cells or hyphae from said culture; and
  (c) combining said spores, cells or hyphae with an agriculturally acceptable carrier, diluent or adjuvant.

According to the above aspects and embodiments, the active ingredient of the composition may be produced by the *Streptomyces* of the present disclosure and secreted into the cell culture. In an exemplary embodiment, the composition comprises the cell free culture filtrate of a *Streptomyces* MH71 and/or MH243 culture. The cell free culture filtrate may be combined with an agriculturally acceptable carrier, diluent or adjuvant. In an embodiment, the active ingredient is one or more metabolite(s). In another embodiment the active ingredient is one or more antibiotics.

A sixth aspect of the present disclosure provides a composition produced by:
  (a) growing a culture of *Streptomyces* MH71 or MH243;
  (b) optionally harvesting the cell free culture filtrate; and
  (c) combining the culture of (a) or the cell culture filtrate of (b) with an agriculturally acceptable carrier, diluent or adjuvant.

In accordance with the above aspects, in an embodiment the composition may also include other agents or organisms capable of treating or preventing an infection or disease caused by, or associated with, a plant pathogen, and/or capable of promoting growth of the plant to which the composition is to be applied. Examples of such agents or organisms include other *Streptomyces* species, or other bacterial species, biocontrol fungal species, germination promoters, fungicides, insecticides, additives and inert carriers as discussed above, provided they are compatible with the survival and growth of the *Streptomyces* MH71 or MH243.

In an embodiment, the composition is used to treat or prevent an infection or disease caused by, or associated with, a plant pathogen. In an embodiment, the composition is used to reduce the susceptibility of a plant to a plant pathogen infection. In an embodiment, the composition is preferably applied to a plant, plant part, plant seed, or plant surrounds to treat or prevent disease caused by, or associated with a plant pathogen, or to reduce the susceptibility of a plant to a pathogen infection.

The composition may be present in a liquid form suitable for immersion or impregnation of plant parts or as a spray. In an embodiment, the plant part is the root or leaves of the plant. In an embodiment, the composition is in the form of a foliar spray. In another embodiment, the composition for use as a spray comprises an adjuvant, including for example an esterified vegetable oil, vegetable oil or emulsifier or combination thereof (e.g. Hasten™).

The composition may also be in the form of an emulsion, paste or powder to enable coating of plant parts, including seeds, or in a granular form for soil application. When used as a seed coating, the composition may also comprise one or more compounds to enable the formulation of a coatable paste. In an exemplary embodiment, the composition suitable for seed application comprises xantham gum.

Accordingly, an seventh aspect of the present disclosure provides a method of treating or preventing a disease caused by, or associated with a plant pathogen infection, or for reducing the susceptibility of a plant to pathogen infection, comprising applying an isolated *Streptomyces* selected from MH71 and MH243 or a composition thereof to the roots, stems, flowers, leaves or seeds of a plant or to plant surrounds, e.g. soil.

In another exemplary embodiment, the composition is applied to the seed of the plant. In a particular embodiment, the composition is applied as a seed coat.

A eighth aspect of the present disclosure provides method of treating or preventing a disease caused by, or associated with a plant pathogen, or for reducing the susceptibility of a plant to a pathogen infection comprising coating the seed of a plant with an isolated *Streptomyces* selected from MH71 and MH243 or a composition thereof.

A ninth aspect of the present disclosure provides a method of treating or preventing a disease caused by, or associated with a plant pathogen, or for reducing the susceptibility of a plant to a pathogen infection, comprising applying an isolated *Streptomyces* selected from MH71 and MH243 or a composition thereof to the roots of a plant.

In an tenth aspect, the present disclosure also relates to methods of treating or preventing a disease caused by, or associated with a plant pathogen, or for reducing the susceptibility of a plant to a pathogen infection, comprising applying a cell free culture filtrate of an isolated *Streptomyces* selected from MH71 and MH243 or a composition thereof to a plant, plant part, seed, or plant surrounds.

In a eleventh aspect, the present disclosure relates to a method of inhibiting or reducing the growth of a pathogen on a plant, the method comprising applying an isolated *Streptomyces* selected from MH71 and MH243 or a composition thereof to the plant, plant part, seed, or plant surrounds.

In a twelfth aspect, the present disclosure relates to a method of inhibiting or reducing the growth of a pathogen on a plant, the method comprising applying a cell free culture filtrate of an isolated *Streptomyces* selected from MH71 and MH243 to the plant, plant part, seed, or plant surrounds.

In accordance with the above aspects, the isolated *Streptomyces*, or a composition or cell free culture filtrate thereof is applied to the leaves, roots, flowers, stem or seeds of the plant or to plant soil.

In an embodiment, the cell free culture filtrate comprises one or more anti-pathogen metabolites. In an exemplary embodiment, the metabolite is an antibiotic and/or enhances the action of an antibiotic in inhibiting or reducing the growth of a pathogen on a plant or plant part, seed or plant surrounds.

In a further embodiment, the cell free culture filtrate may comprise one or more proteins that contribute to the inhibition or reduction of the growth of a pathogen on a plant or plant part, seed or plant surrounds. In an embodiment, the protein has enzymatic activity.

In accordance with the above aspects and embodiments, pathogen growth is inhibited or reduced by about 40%, by about 45%, by about 50%, by about 55%, by about 60%, by about 65%, by about 70%, by about 75%, by about 80%, by about 85%, by about 90%, by about 95% or by about 100%.

In an embodiment, the pathogen is a fungal pathogen. In a particular embodiment, the fungal pathogen is a member of the genus selected from *Sclerotinia, Fusarium, Gaeumannomyces, Leptosphaeria, Pythium, Alternaria* and *Rhizoctonia*. In another exemplary embodiment, the fungal pathogen is one or more of *Sclerotinia sclerotiorum, Fusarium pseudograrninearum, Fusarium oxysporum, Gaeumannomyces graminis, Pythium irregulare, Rhizoctonia solani* AG2-1, *Rhizoctonia solani* AGB, *Blumeria graminis, Leptosphaeria maculans,* and *Alternaria brassicicola*.

In an embodiment, the pathogen is a bacterial pathogen. In a particular embodiment, the bacterial pathogen is a member of the genus selected from *Xanthomonas, Pseudomonas, Ralstonia, Agrobacterium, Erwinia, Xylella, Dickeya, Pectobacterium, Clavibacter* and *Candidatus*. In a particular embodiment, the bacterial pathogen is a member of the genus selected from *Xanthomonas* and *Pseudomonas*. In another exemplary embodiment, the bacterial pathogen is *Pseudomonas syringae, Xanthomonas translucens* or *Xanthomonas oryzae,* optionally *Xanthomonas oryzae* pv. *oryzae*.

In exemplary embodiments, the plant is selected from a crop plant, such as a broad acre crop, horticulture crop, or a crop for fibre production or ornamentals. In particular exemplary embodiments, the plant is wheat or canola.

In a thirteenth aspect, the present disclosure provides a method for reducing the susceptibility of germinating seeds to a pathogenic infection, comprising immersing plant seeds in a composition comprising the *Streptomyces* MH71 or MH243 as described herein, and planting the seeds in a suitable growth medium under conditions suitable for germination.

The *Streptomyces* MH71 or MH243 as described herein maintain the growth of a plant and/or yield of a plant crop which has been exposed to, is infected with or which is susceptible to a plant pathogen, at levels the same or similar to the growth of a plant or plant crop which has not been exposed to, infected with or which is not susceptible to the plant pathogen.

Accordingly, a fourteenth aspect of the present disclosure provides a method for maintaining plant growth and/or yield of a plant crop, wherein the plant or plant crop has been exposed to, infected with or which is susceptible to a plant pathogen, the method comprising applying to the plant, plant part, seed, or plant surrounds, a *Streptomyces* or composition thereof as herein described, wherein the growth of the plant and/or yield is the same or substantially the same as the growth of a control plant or yield of a plant crop, which has not been exposed to, infected with or which is not susceptible to the pathogen.

In a fifteenth aspect of the present disclosure, methods are provided for obtaining an antifungal metabolite, such as an antibiotic compound, which effectively reduces or inhibits the growth of a plant pathogen. This method comprises culturing the purified *Streptomyces* MH71 or MH243 as described herein under conditions sufficient to allow the production of an antifungal metabolite or metabolites, such as an antibiotic compound, harvesting the culture medium containing the antifungal metabolite(s)/compound(s); and optionally filtering the culture medium to obtain a cell free culture filtrate.

The following disclosure relates to all the above aspects and embodiments.

BRIEF DESCRIPTION OF THE DRAWINGS

Embodiments of the invention are described herein, by way of non-limiting example only, with reference to the following figures.

DETAILED DESCRIPTION

Figure 1:
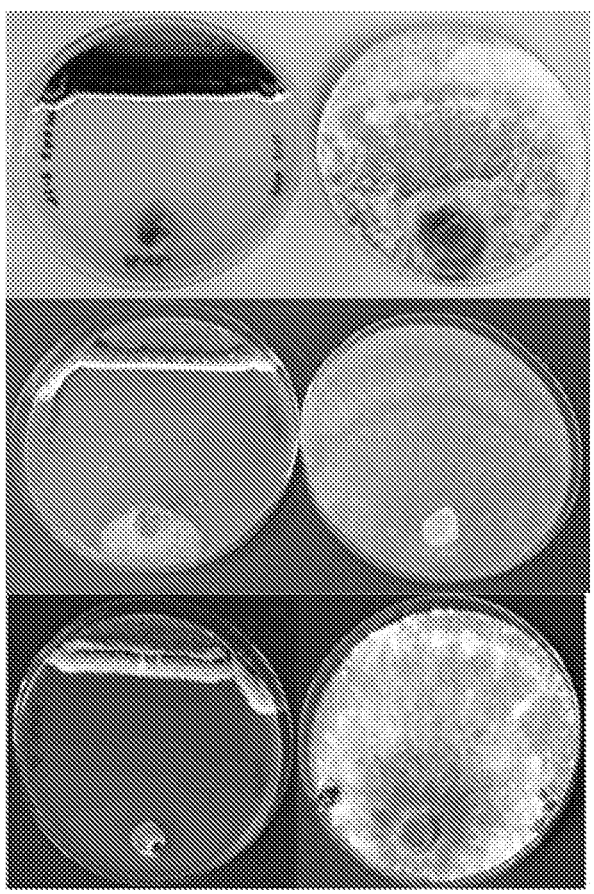
FIG. 1. Shows the results of in vitro suppression of fungal pathogens by Actinobacteria. In each pair of images, the plate on the left is inoculated with the antifungal Actinobacteria isolate at the top of the plate and the fungal pathogen at the bottom of the plate while the plate on the right is inoculated with the fungal pathogen only at the bottom of the plate. Top image shows Streptomyces MH243 suppressing Fusarium pseudograrninearum (crown rot), middle image shows MH243 suppressing Rhizoctonia solani AG2-1 (hypocotyl/root rot) and bottom image shows MH71 suppressing Sclerotinia sclerotiorum (Sclerotinia stem rot).

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, typical methods and materials are described.

The articles "a" and "an" are used herein to refer to one or to more than one (i.e., to at least one) of the grammatical object of the article, unless the context clearly dictates otherwise. By way of example, "a strain" can mean one strain or more than one strain.

In the context of this specification, the term "about," is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The present disclosure is predicated on the inventors' surprising isolation of new Actinobacteria strains belonging to the Streptomyces genus, designated MH71 and MH243, which are highly effective at preventing or reducing the growth of a broad range of pathogens in plants. The present inventors have also found that application of MH71 and/or MH243 to a plant exposed to a plant pathogen, results in plant growth and development which is the same or substantially the same as the growth and development of a control plant which has not been exposed to the plant pathogen. Thus, the isolated Streptomyces strains are useful in methods for reducing the susceptibility to, or for treating or preventing, a disease caused by or associated with a plant pathogen.

The new *Actinobacteria* strains have been deposited in the National Measurement Institute Laboratories (NMI), Bertie Street, Port Melbourne, Victoria, Australia according to the Budapest Treaty for the purposes of patent procedure. The isolates have been accorded deposit numbers V17/004100 and V17/004101 respectively.

Details of the isolation and selection process employed to obtain the isolates are set out in the Examples.

Thus, a first aspect of the present disclosure provides *Streptomyces* strain MH71 deposited with the National Measurement Institute (NMI), Australia on 21 Feb. 2017 under Accession Number V17/004100.

A second aspect of the present disclosure provides *Streptomyces* strain MH243 deposited with the National Measurement Institute (NMI), Australia on 21 Feb. 2017 under Accession Number V17/004101.

In accordance with the above aspects, the *Streptomyces* strains MH71 and MH243 are preferably in an isolated form. As used herein, an "isolated" strain is a strain that has been separated from materials with which it is normally associated in nature (e.g. soil). Although the strain or strains may be present in combination with other bacteria of the same or a different genus, whether the bacteria are brought together by hand of man and co-cultured, or whether bacteria existing together in nature are partially purified from other bacteria with which they exist in nature.

As such, the term "isolated" does not necessarily reflect the extent to which the strain has been purified. Further, a strain associated with other strains, or with compounds or materials that it is not normally found with in nature, is still defined as "isolated".

Typically, the MH71 and/or MH243 strains are in a culture. In exemplary embodiments, the MH71 and/or MH243 strains are in a pure or substantially pure culture.

The term "culture" as used herein refers to both liquid and plate cultures. "Culturing", as used herein, refers to the propagation of organisms on or in media of various kinds.

A "pure" culture is a population of organisms growing in the absence of other species or types. A "substantially pure culture" of the strain or strains refers to a culture which contains substantially no other microbes than the desired strain or strains. In other words, a substantially pure culture is substantially free of other contaminants, which can include microbial contaminants as well as undesirable chemical contaminants.

Plant diseases that are preventable or treatable in accordance with the present disclosure can result from any pathogen. As used herein, the term "pathogen" is to be understood to refer to any organism that causes disease in plants. Illustrative examples include pathogenic bacteria, fungi, moulds, parasites such as nematodes and viruses specific to plant species which are responsible for induction of disease symptoms. In a particular embodiment of the disclosure, the pathogen is a soil or stubble-borne pathogen. In exemplary embodiments, the pathogen is a fungal pathogen.

As used herein the term "plant" is to be understood to refer to any member of the kingdom Plantae and any other photosynthetic plant-like organism such as algae. In particular, the term "plant", as used herein, refers to any plant which is prone to a disease caused by, or associated with, a pathogen.

In the context of the application of the *Streptomyces* strains or compositions thereof in accordance with the present disclosure, the term "plant" includes within its meaning a whole plant, any reproductive or developmental form or stage thereof, or to a part or fragment of a plant. The term "plant" may therefore be used to encompass plant propagules, seedlings, germinants, tube stock and mature plants or any parts or fragments thereof, including but not limited to hypocotyls, leaves, branches, stems, roots, heads/kernels, crown, tissue samples, seeds, fruits, nuts, flowers or cones.

Reference to "seed" and "seeds" is used interchangeably herein and means seeds, typically viable seeds, to which compositions in accordance with the present disclosure may be applied. It should also be understood that reference to a "seed" as provided herein means seeds that are capable of germinating to at least conventional levels of germination typical of the relevant plant species under consideration.

Reference to "maintaining plant growth" as used herein means that the growth of a plant or parts thereof (such as roots and shoots) which has been exposed to, infected with or which is susceptible to a pathogen, is the same or substantially the same as compared to a control plant or parts thereof which has not been exposed to, infected with or which is not susceptible to a pathogen, or as compared to a predetermined standard. Alternatively, "maintenance of plant growth" can be determined by recording differences in biomass between a plant or parts thereof which has been exposed to, is infected with or which is susceptible to a pathogen, as compared to the biomass of a control plant or parts thereof which has not been exposed to, infected with or which is not susceptible to a pathogen, or as compared to a predetermined standard.

The term "plant biomass" as used herein means biological material derived from a living, or recently living plant. Methods for measuring plant biomass may be employed, for example, by taking samples of plant tissues (which may be roots, shoots, leaves, heads or grains) and drying at +60° C. until the mass no longer changes upon further drying. Without being limited by anyone theory or mode of action, plant biomass is generally taken on replicate samples (minimum 3) and presented as the mean dry mass+/−standard error of the mean. The dry mass can be used individually as "tissue biomass" or summed to give "above ground biomass", "below ground biomass" or "total biomass".

In the context of the present specification "maintaining the yield" of a plant crop is to be understood to refer to an increase in any measure of output (typically agricultural or horticultural output) from the crop including, by way of example only, maintaining the biomass of the plant or one or more plant parts (such as edible plant parts), or maintaining plant growth, such as for example, maintaining the number, size, volume, viability or quality of one or more plant parts such as fruit, vegetable, tuber, seed, nut, flower, stalk, stem, leaf or any other plant part that has economic value as compared to a control.

In the context of the present specification, the terms "decreasing", "reducing", "inhibition" and the like when used in relation to any parameter of pathogen growth, development, function or behaviour following the application to a plant of a *Streptomyces* isolate in accordance with embodiments of the present disclosure, will be understood to refer to an decrease, reduction or inhibition of the selected parameter as a result of the application when compared to the absence of the application.

The term "plant surrounds" refers to the soil or other media in which the plant is growing or maintained and which is in the immediate vicinity of the plant, such that upon application, the active agent(s) are capable of reaching and contacting the roots of the plant.

As used herein the terms "treating", "treatment", "preventing" and "prevention" refer to any and all uses which remedy a disease condition or symptoms caused by or associated with a pathogen infection, prevent the establishment of a disease caused by or associated with a pathogen infection, or otherwise prevent, hinder, retard, or reverse the progression of a disease or other undesirable symptoms caused by or associated with a pathogen infection in any way whatsoever. Thus the terms "treating" and "preventing" and the like are to be considered in their broadest context. For example, treatment does not necessarily imply that the plant is treated until total recovery. In conditions which display or are characterized by multiple symptoms, the treatment or prevention need not necessarily remedy, prevent, hinder, retard, or reverse all of said symptoms, but may prevent, hinder, retard, or reverse one or more of said symptoms. In the context of some plant diseases caused by or associated with a pathogen infection, methods of the present invention involve "treating" the disease in terms of reducing or ameliorating the occurrence of a highly undesirable event associated with the disease or an irreversible outcome of the progression of the disease but may not of itself prevent the initial occurrence of the event or outcome. Accordingly, treatment includes amelioration of the symptoms of a particular disease or preventing or otherwise reducing the risk of developing a particular disease.

As used herein the terms "treat", "treatment", "preventing" and "prevention" should also be understood to refer to the process of suppressing, inhibiting, or reducing the growth of a plant pathogen.

As used herein reference to "reducing the susceptibility" of a plant to a pathogenic infection should be understood to refer to the process of protecting the plant from infection by a plant pathogen, including protecting a healthy plant free from disease. It should be understood that a reduction in susceptibility does not necessarily imply that a plant will no longer develop a pathogenic infection. Rather a reduction in susceptibility means that the likelihood that a plant will develop a disease caused by or associated with a pathogen infection is less than the likelihood that a plant which has not undergone treatment will develop a disease caused by or associated with a pathogen infection.

In an embodiment, pathogen growth is inhibited or reduced by about 40%, by about 45%, by about 50%, by about 55%, by about 60%, by about 65%, by about 70%, by about 75%, by about 80%, by about 85%, by about 90%, by about 95% or by about 100%.

The present disclosure provides an effective, simple, economical means for controlling disease caused by, or associated with a pathogen in plants and of maintaining plant growth and/or crop yield by reducing plant pathogen load and enabling plants to survive and grow even in disease prone environments which has the particular benefit of reduced or minimal harm upon ecosystems or the environment.

Fungal plant diseases in particular cost the Australian grain and oilseed industries millions of dollars in lost revenue each year. Current management strategies have limited effectiveness against plant fungal pathogens including, for example, those from the genus *Fusarium, Gaeumannomyces, Rhizoctonia, Pythium, Sclerotinia, Alternaria,* and *Blumeria*. As noted elsewhere, the inventors have surprisingly found that a composition comprising *Streptomyces* isolates MH71 and MH243 applied to plants, including plant seeds, exhibited a high biofungicide efficacy against a broad range of plant fungal pathogens.

In a particular embodiment of the disclosure the pathogen is a fungal pathogen. Illustrative examples of fungal pathogens contemplated by the present disclosure include, but are by no means limited to, those pathogens belonging to the *Fusarium* spp. (e.g. causal agents of *Fusarium* wilt disease, *Fusarium* crown rot disease and *Fusarium* head blight), *Gaeumannomyces graminis* (e.g. causal agent of take-all root rot), *Leptosphaeria maculans* (e.g. causative agent of blackleg), *Sclerotinia sclerotiorum* (e.g. causal agents of *Sclerotinia* stem rot, also known as white mould/mold, cottony rot; watery soft rot; and blossom blight), *Alternaria* spp. (e.g. *A. brassicicola* blight), *Ustilago* spp. (e.g. the causal agents of smut), *Rhizoctonia* spp. (e.g. causal agents of root and hypocotyl rot and of barepatch), *Pythium irregulare* (e.g. causal agent of *Pythium* root rot), *Thielaviopsis* spp. (e.g. causal agents of canker rot, black root rot, *Thielaviopsis* root rot), *Verticillium* spp., *Magnaporthe grisea* (e.g. causal agent of rice blast), *Phakospora pachyrhizi* (e.g. causal agent of soybean rust), *Puccinia* spp. (e.g. causal agents of severe rusts of virtually all cereal grains and cultivated grasses), *Blumeria graminis* (powdery mildew of wheat), *Erysiphe* spp. (e.g. *Erysiphe necator* causal agent of powdery mildew of grapes), *Botrytis cinerea* (causal agent of *botrytis* bunch rot and grey mould/gray mold) and *Armillaria* spp. (e.g. the so-called honey fungus species, which are virulent pathogens of trees and produce edible mushrooms).

Illustrative examples of plant diseases that are mediated by a *Sclerotinia* species, which are treatable in accordance with the present invention include *Sclerotinia sclerotiorum*.

Illustrative examples of plant diseases that are mediated by a *Fusarium* species, which are treatable in accordance with the present invention include *Fusarium pseudograminearum, Fusarium graminearum,* and *Fusarium oxysporum* infection.

Illustrative examples of plant diseases that are mediated by a *Gaeumannomyces* species, which are treatable in accordance with the present invention include *Gaeumannomyces graminis* infection.

Illustrative examples of plant diseases that are mediated by a *Rhizoctonia* species, which are treatable in accordance with the present invention include *Rhizoctonia solani* infection.

Illustrative examples of plant diseases that are mediated by a *Pythium* species, which are treatable in accordance with the present invention include *Pythium aphanidermatum, Pythium irregulare,* and/or *Pythium ultimum* infection.

The inventors have also found that a composition comprising cell-free extracts from *Streptomyces* isolates MH71 and MH243 exhibit high efficacy against plant bacterial pathogens.

Illustrative examples of bacterial pathogens contemplated by the present disclosure include, but are by no means limited to those pathogens belonging to the genus selected from *Xanthomonas* (e.g. *Xanthomonas oryzae* pv. *oryzae; Xanthomonas campestris* pathovars; *Xanthomonas translucens* pathovars; and *Xanthomonas axonopodis* pathovars), *Pseudomonas* (e.g. *Pseudomonas syringae* pathovars; and *Pseudomonas fuscovaginae*), *Ralstonia* (e.g. *Ralstonia solanacearum*), *Agrobacterium* (e.g. *Agrobacterium tumefaciens*), *Erwinia* (e.g. *Erwinia amylovora*—also known as fireblight), *Xylella* (e.g. *Xylella fastidiosa*), *Dickeya* (e.g. *dadantii* and *solani*), *Pectobacterium* (e.g. *Pectobacterium carotovorum* and *Pectobacterium atrosepticum*), *Clavibacter* (e.g. *Clavibacter michiganensis* (ring rot) and *Clavibacter sepedonicus*) and *Candidatus* (e.g. *Candidatus Liberibacter asiaticus*).

The potential to treat or prevent plant disease caused by, or associated with a pathogen, and to reduce the susceptibility of a plant to a pathogen infection, has significant potential commercial and environmental benefits including in broad acre crop production, horticulture for food or fibre, ornamentals, native ecosystem establishment and rehabilitation, plantation forestry, mine site restoration, landscaping, agriculture, plant propagation in nurseries, and other related industries. Therefore, the present disclosure may be applied to any plant species. These benefits may manifest in plants grown under a variety of conditions (including, for example, field, glasshouse, container or vat grown).

Accordingly, in accordance with the present disclosure, the plant species may be a monocotyledon or dicotyledon and may be evergreen or deciduous. The plant may be a grass or cereal, e.g. wheat, barley, corn, oats, rice, rye, sorghum, maize, millet; a herb; a fruit tree such as, for example citrus, apple, avocado, coconut, pear, date palm; an oilseed plant including soybeans, sunflowers, rapeseed (canola), cotton, peanuts, flax (linseed) and castor beans; a pulse crop such as chickpea, faba/broad bean, field pea, lentil, lupin and mungbean, azuki bean, navy bean, cowpea, vetch and pigeon pea; a vegetable such as from Fabaceae (pea family) e.g. peas, beans, lentils; Solanaceae (nightshade family) e.g. tomatoes, eggplants, bell peppers, potatoes; Brassicaceae (mustard family) e.g. cauliflower, cabbage, brussels sprouts, broccoli; Allium family e.g. onions, garlic, leek, shallot, chives; Carrots (Apiaceae); Lettuce (Asteraceae); cucurbit family of plants including melon, cantaloupe, cucumber, calabash, squash, and pumpkin; a herbaceous flowering plant from the genus Musa e.g. banana, a horticultural flowering plant, or a woody plant species (e.g., CAM, C3 and C4 plant species) including but not limited to eucalypts, pine, spruce, willow, etc.; or other crop species such as, for example, cotton, coffee, tea. The listed plant species are provided by way of illustration only, and the scope of the present disclosure will be understood to not be limited to the illustrations provided. Also by way of illustration, where the disclosure is employed for revegetation of mine sites, the plants may be grasses or woody plant species, such as eucalypts, e.g., *Corymbia maculata* (spotten gum), *Acacia falcata, Eucalyptus tereticornis* (forest red gum), and *Eucalyptus camaldulensis* (river red gum). Other commercially relevant species include Sitka willow (*Salix sitchensis*), Sitka alder (*Alnus viridis*), Jack pine (*Pinus banksiana*), White spruce (*Picea glauca*), Lodgepole pine (*Pinus contorta*). The present disclosure also contemplates the employment of methods disclosed herein in relation to biofuel crops such as, for example green algae (such as *Chlorella protothecoides*), sugar cane, sunflower and soybean.

In exemplary embodiments, the plant is a crop plant or oil seed plant. In an embodiment, the plant is selected from wheat and canola.

Phylogenetically, *Streptomyces* belong to the phylum *Actinobacteria*, also known as Actinomycetes, which are a group of Gram-positive bacteria whose genetic material (DNA) is GC-rich (70%) when compared with other bacteria such as *Escherichia coli* (50%). *Streptomyces* grow in various environments, and its shape resembles filamentous fungi. *Actinobacteria* reproduce via spores; more specifically, hyphal growth is followed by fragmentation and release of spores. The morphological differentiation of *Streptomyces* involves the formation of a layer of hyphae that can differentiate into a chain of spores.

Accordingly, as used herein, reference to a *Streptomyces* isolate in accordance with the recent disclosure, should also be understood as reference to parts of the *Streptomyces* which are reproductively viable, for example but not limited to spores and hyphae.

In the context of the present disclosure, the *Streptomyces* isolates can be formulated in a composition suitable for application to a plant, plant part, a plant seed, or the plant surrounds (e.g. soil) in which the plant is growing or will be grown.

As described and exemplified herein, the present inventors have made the surprising and advantageous discovery that a cell free culture filtrate of the *Streptomyces* isolates disclosed herein inhibited or reduced the growth of a broad range of fungal and bacterial pathogens. Application of the cell free culture filtrate to a plant protected the plant from or reduced infection by these pathogens.

Accordingly, compositions suitable for use in accordance with the present disclosure can also be prepared, using a cell free filtrate material derived from a *Streptomyces* microorganism culture.

A cell free culture may be prepared using one or more of the methods well known to the person skilled in the art. In particular examples, the *Streptomyces* isolate identified in accordance with the present disclosure is inoculated from an agar slant to a suitable nutrient medium and grown to late log phase. For example, the cultures are grown on half-strength potato-dextrose agar plates for at least 3 weeks (until the black glossy colouration appears on the colonies). To make the filtrate a sterile loop is used to pick colonies and inoculate sterile YME broth (pH 7.2). Alternatively the YME broth can be inoculated directly with spores from a water spore suspension. After some 4-6 weeks of growth in culture the bacterial cells are harvested by passing the solution through a miracloth filter and the supernatant ("culture filtrate") is filter-sterilized through 0.2 μm filter to remove remaining cells. The culture filtrate is thereafter freeze-dried and reconstituted, in concentrate form, in deionized water. The culture filtrate can then be filter-sterilized and diluted to an appropriate concentration for testing, described above. In another example, the cell free filtrate can be diluted (e.g. 1 in 10) in sterile water without freeze drying. For spraying, additives which increase wettability, spreading and/or which modify droplet formation and behaviour such as, for example, an adjuvant, are added to the resulting solution.

Without wishing to be bound by theory, a property of *Streptomyces* is the ability to produce bioactive secondary metabolites such as antifungals, antivirals, antitumoral, antihypertensives, and mainly antibiotics and immunosuppressives. The production of most antibiotics is species specific, and these secondary metabolites are important so the *Streptomyces* spp. can for example, compete with other microorganisms that they may come in contact with.

Accordingly, in an embodiment of the disclosure the cell free culture comprises metabolites secreted by the *Streptomyces* isolates disclosed herein.

The term "metabolite" as used herein refers to any compound, substance or by-product of a fermentation of a microorganism that has biocidal activity. In the case of some bacteria, its growth phase can be bifurcated into a primary metabolic phase and a secondary metabolic phase. The secondary phase metabolites are metabolites that are produced after bacterial active stage of growth. In an embodiment, the metabolite is an antibiotic. In another embodiment, the metabolite is an agent which enhances the action of an antibiotic in inhibiting or reducing the growth of a pathogen on a plant or plant part, seed or plant surrounds.

As used herein the term "applied", "applying" or "application" when used in relation to application of the *Streptomyces* isolates described herein or a composition thereof, will be understood to refer also encompass "contacting" the plant, plant part, seed and/or soil the plant is to be grown in, is growing in or plant surrounds, with the *Streptomyces* isolate or composition thereof, as well as to "inoculating" a plant, plant part, or seed, with the *Streptomyces* isolate or composition thereof.

The term "inoculating a plant" with a the *Streptomyces* isolate or composition thereof, for example, as used herein refers to the process of applying to or contacting a plant (including its roots, stem, leaves or seeds) with, the *Streptomyces* isolate or composition thereof.

*Streptomyces* may be prepared for use in the compositions of the invention using standard techniques known in the art, for example static drying and liquid fermentation. The *Streptomyces* can be produced/grown using one or more of the methods well known to those skilled in the art, including, for example, the use of a bioreactor.

A bioreactor refers to any device or system that supports a biologically active environment. As described herein a bioreactor is a vessel in which microorganisms including *Streptomyces* can be grown. For small scale operations, a batch bioreactor may be used, for example, to test and develop new processes, and for processes that cannot be converted to continuous operations.

Microorganisms grown in a bioreactor may be suspended or immobilized. Growth in the bioreactor is generally under aerobic conditions at suitable temperatures and pH for growth. The skilled person can easily determine the optimum growth conditions required (e.g. temperature, nutrient concentration, pH and dissolved gases) using knowledge in the art. In an example, typical growth temperatures are from 25-30° C. and the pH of the growth medium is usually about 7.2.

Growth medium may be any known art medium suitable for culture of *Streptomyces* species, such as Yeast Malt Extract (YME), Starch casein agar (SCA) medium, Actinomycete Isolation Agar Himedia®. The strains when grown under these conditions generally produce hyphae within a week and spores within 2-3 weeks. The cell culture, spores or hyphae may be harvested using conventional washing, filtering or sedimentary techniques such as centrifugation, or may be harvested dry using a cyclone system, for example a MycoHarvester MKV (MycoHarvester, Bateman, Berks, UK). In another example, spores may be harvested off mature plates by scraping with a sterile blade or inoculation loop.

The cell culture, spores or hyphae can be used immediately or stored using standard conditions known in the art, for example the cell culture, spores or hyphae can be stored at room temperature in water suspensions and coated onto seeds, for a period of >12 months. In another example, the cell culture, spores or hyphae can be stored under chilled conditions (such as, 1° C. to 10° C., 1 to 7° C., 2 to 4° C. or 2° C.), or may be freeze dried. Dried cell culture, spore or hyphae preparations can be used for as long as they remain reproductively viable.

Compositions suitable for use with the present disclosure may be in liquid or solid form. The spore and/or hyphae containing growth medium discussed above is a liquid. This liquid can be used per se, for example, as a dip or spray to inoculate seeds, plants, soils, pastures, or turf. Seeds coated with the liquid composition may be subsequently dried and stored for future use.

The liquid composition may be further formulated with an agriculturally acceptable diluent or carrier to form a spray, foam, drench, slurry, gel, dip, emulsion or paste and optionally combined with co-formulants or nutrient amendments such as seaweed. Suitable carriers include water, aqueous solution, slurries, granules, or powders.

In one embodiment the composition is in solid form. This composition may be produced by drying of the liquid compositions of the present disclosure. Alternatively, a solid composition useful herein may be produced by combining *Streptomyces* bacteria, or cells, spores or hyphae thereof with an agriculturally acceptable carrier such as seed, lime, kaolin, maize chip, humate and diatomite or mixtures thereof. One preparation comprises a powdered form of the composition which may be dusted onto plants.

In one embodiment the solid composition is prepared in the form of pellets or prills using known art techniques. In one embodiment prill production involves coating the *Streptomyces* of the present disclosure in any appropriate rotary mixing bowl.

In accordance with the present disclosure the *Streptomyces* or composition comprising the *Streptomyces* may be applied alone, or in combination with other additives, such as, but not limited to, surfactants, adjuvants, wetting agents, humectants, stickers, spreaders, stabilisers, penetrants to enhance activity, stressing agents to improve spore vigour, U.V. protectants and plant-protecting substances, or mixtures thereof. Such additives may be applied separately to the same or different part of the plant being treated with the *Streptomyces* and may be applied at the same time, before or after treatment with the *Streptomyces*. In another embodiment, such additives may be included in a composition comprising the *Streptomyces* species.

Examples of plant-protecting substances, include, for example, chemical fertilizer, insecticide, fungicide, nematicide, organic fertilizer, herbicides, nutrients, or micronutrients. Examples of stressing agents include potassium chloride, sodium chloride, glycerol and glucose.

Reference to an "adjuvant" as used herein includes any additive that has the function of improving, modifying, or aiding the activity or application characteristics of the composition comprising the *Streptomyces* isolates defined herein. For example, in relation to an aqueous solution, an adjuvant may function to improve the spreadability and/or wettability of the composition, or to modify droplet formation and/or behavior.

Examples of adjuvants that may be included in an aqueous solution to be applied to a plant include, for example, esterified oil (e.g. esterified vegetable oil), vegetable oil, anionic, cationic, non-ionic or amphiphilic surfactants, which may be used to improve dispersibility, wettability, penetration and/or translocation, and for effecting miscibility and stability of the preparation in a ready-to-use dilution. The adjuvant may be a mixture of the above, for example, an esterified oil based product with non-ionic surfactants. In an embodiment, the adjuvant comprises a combination of an esterified vegetable oil and a surfactant. An example, of one such adjuvant is Hasten™.

The composition may also comprise other adjuvants, such as pH modifiers, carriers, anti-foaming agents, thickening agents, anti-freezing agents, organic solvents (preferably water-miscible solvents), preservatives, and colouring agents. In solid forms, such as granules, powders and tablets inert inorganic (e.g., silica, salts) or organic (e.g., cellulose, polyacrylates, urea) compounds may be employed as carriers for diluting the organic acid or adsorbing moisture. Such solid forms may be prepared by a variety of standard methods known to those skilled in the art, for example, by disc granulation, spray drying, fluidized bed granulation, mixing granulation by a vertical mixer or paddle mixer, or by extrusion, compacting, centrifugal jet layer, or spraying/cooling granulation.

In a particular example, when applied as seed coats the Actinobacterial spores are mixed with xanthan gum and applied directly to seeds without any other additives.

Additives may also include compositions which assist in maintaining microorganism viability in long term storage, for example unrefined corn oil and so called invert emulsions containing a mixture of oils and waxes on the outside and water, sodium alginate and conidia on the inside. Examples of surfactants, spreaders, penetrants, and stickers include Fortune®, Pulse®, C-Daxoil®, Codacide Oil®, D-C. Tate®, Supamet Oil, Bond®, Citowett® and Freeway®. Where selected for inclusion, common agricultural surfactants, such as Hasten™ are desirably included in the composition according to known protocols. This list of additives is for illustrative purposes only. It is important that any additives used are present in amounts that do not interfere with the effectiveness of the *Streptomyces* strains exemplified herein.

The compositions in accordance with the present disclosure, in whatever form may also include acidulants, alginates, mannans, glycerol, polysaccharides, cellulose, xylans, carageenans, nutrients, trace elements, minerals, proteins, fats, soluble carbohydrates, insoluble carbohydrates and vitamins, and additives to extend shelf life.

In one embodiment, the prill includes maize chip, diatomite, humate and nutrient mix. The nutrient mix contains soluble and insoluble carbohydrates, protein, fats and trace elements commonly employed in prills. The pellets or prills are particularly useful for sowing into new pastures or over-sowing of older established pastures.

In accordance with the above aspects, in an embodiment the composition may also include other agents or organisms capable of treating or preventing an infection or disease caused by, or associated with, a plant pathogen, and/or capable of promoting growth of the plant to which the composition is to be applied. Examples of such agents or organisms include other *Streptomyces* species, or other bacterial species, biocontrol fungal species, germination promoters, fungicides, insecticides, additives and inert carriers as discussed above, provided they are compatible with the survival and growth of the *Streptomyces* MH71 or MH243.

Similarly, any of the carriers, diluents, adjuvants and additives used in the compositions of the invention should not be phytotoxic, or bactericidal.

As used herein the term "effective concentration" includes within its meaning a non-toxic but sufficient amount of a *Streptomyces* isolate disclosed herein or composition thereof, or cell free culture filtrate to provide the desired effect. The exact concentration required will vary from application to application depending on factors such as: the species of plant being treated; the age and general condition of the plant; whether the plant is treated prior to planting or in situ; soil conditions such as soil type, salinity, water content, acidity, nutrient levels and organic matter composition; climactic factors such as temperature and rainfall; the mode of application; the form in which the composition is applied, the identity and number of pathogens infecting the plant, the identity and number of individual isolates in the composition, the severity of infection or disease at the time of administration and so forth. Thus, it is not possible to specify an exact "effective concentration". One of skill in the art can readily determine the amount or concentration of the *Streptomyces* isolate or composition thereof, or cell culture filtrate that should be applied to the plant or plant seed and/or plant soil to treat, prevent or reduce susceptibility to a disease caused by a pathogen, and/or to promote plant growth.

To apply a composition comprising the *Streptomyces* to a plant in accordance with the present disclosure, any method suitable for the purpose may be used. The composition comprising one or more of a *Streptomyces* isolate as disclosed herein can be applied to the plant by dry or wet formulation for example, as a liquid, powder, emulsion or paste. The application method will typically depend on the plant part which is to be treated for or which is susceptible to, pathogen infection. For example, a xanthan gum based seed coat is used for treating or preventing root diseases and an aqueous spray, including an adjuvant or surfactant to help improve leaf wetting, is used for foliar diseases.

In accordance with the present disclosure, an aqueous solution comprising the *Streptomyces* isolates disclosed herein or a composition thereof may be applied directly to the plant, seed or plant growth medium (e.g., plant surrounds, such as soil, potting mix, hydroponic medium). The plant may be treated, for example, by application of an aqueous solution comprising the *Streptomyces* to the foliage, flowers, stem or base of the plant, to a plant propagule or to the plant roots. In an embodiment the *Streptomyces* or composition thereof is applied to the leaves or roots. In a particular embodiment, the plant may be treated by spraying a liquid composition comprising the microorganism onto the leaves of the plant. In an embodiment, the roots of a plant are soaked in a liquid solution comprising the *Streptomyces* isolate or a composition thereof.

In a particular embodiment the *Streptomyces* isolates disclosed herein or composition thereof is applied to a plant propagule such as a seed. In a particular embodiment, plants or plant propagules may be treated prior to planting in the plant growth medium (e.g., soil) in the location where they are to be grown, for example, as seeds, seedlings, young germinants, tube stock, or other form of potted plant. In a particular embodiment of the disclosure, treating the plant takes place prior to planting by soaking or contacting the seed with a solution (typically an aqueous solution) comprising the *Streptomyces* isolates or a composition thereof. In a particularly preferred embodiment, the seed is coated with the composition.

In an alternative embodiment, plants or plant propagules may be treated when planted in the location in which they are to be grown (i.e. in situ).

In another embodiment, the *Streptomyces* isolates or a composition thereof may be applied to the soil, e.g. as a powder or granules, then watered into the soil. In one embodiment, for application to soil, pastures, or turf, pellets or prills are sown into soil with seed, or over sown into pastures or turf with or without seed. In an alternate embodiment the *Streptomyces* isolates or compositions thereof in accordance with the present disclosure are applied to existing pastures or turf in the form of a wettable powder as a root drench.

The skilled addressee will appreciate that the compositions of the present disclosure may also be added direct to the soil or growing medium into which plants as herein defined are to be planted. Such compositions may be added as powders and mixed with the soil or applied as liquid suspensions using conventional procedures.

As used herein, the term "plant soil" should be understood to include the soil in which the plant is currently growing, including pastures and turf, as well as the soil in which the plant is to be grown, including pastures and turf.

The compositions disclosed herein may be applied to the foliage by high or low pressure spray application. Foliar application can also be carried out by coating, immersion, or dusting. The compositions and *Streptomyces* isolates disclosed herein can also be used in hydroponic systems including soilless bags, and rockwool.

It should be understood that the methods and uses described herein for application of the *Streptomyces* isolates described herein or a composition thereof, apply to all methods and uses of the disclosure described, for example, for treating or preventing a disease caused by, or associated with a plant pathogen, reducing the susceptibility of a plant to a plant pathogen as well as the maintenance of plant growth, and/or plant crop yield in the presence of a plant pathogen.

Also encompassed are plants, soils and seeds treated with one or more *Streptomyces* isolates or a composition thereof in accordance with the present disclosure.

Without wishing to be bound by theory, pathogen infection of susceptible untreated plants affects certain growth characteristics of such plants. For instance, untreated plants exposed to plant pathogens may show significant reductions in plant height, plant biomass and crop yield compared to plants not exposed to the pathogen. As exemplified herein, plants exposed to, infected with, or susceptible to a plant pathogen and treated with the *Streptomyces* isolates MH71 and MH243 demonstrated similar root and shoot growth and/or biomass as compared to a control plant which has not been exposed to, infected with, or which is not susceptible to a plant pathogen.

Accordingly, in an embodiment of the present disclosure, plants treated with the *Streptomyces* isolates MH71 and MH243 or compositions thereof, and subsequently exposed to a pathogen, show less severe reductions in plant height, plant biomass and/or crop yield than untreated plants exposed to the pathogen.

In a particular embodiment, a plant treated with the *Streptomyces* isolates of the present disclosure or compositions thereof and exposed to a pathogen will show growth characteristics similar to untreated plants not exposed to a pathogen.

It will be appreciated that the above described terms and associated definitions are used for the purpose of explanation only and are not intended to be limiting.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

The present disclosure will now be described with reference to the following specific examples, which should not be construed as in any way limiting the scope of the invention.

EXAMPLES

The following examples are illustrative of the methods disclosed herein and should not be construed as limiting in any way the general nature of the disclosure of the description throughout this specification.

Example 1

Collection and Isolation of Endophytic *Actinobacteria*

*Actinobacteria* were isolated from the roots of healthy wheat plants in the Western Australia wheat belt. Plants were selected from areas of paddocks that had shown anecdotal evidence of superior growth and yield, and less disease compared to other areas on the same farm with no obvious environmental or climatic explanation. Plants were sampled at random from these areas by hand picking to collect roots as well as shoots. Upon return to the laboratory, plant roots were surface sterilised by washing roots in 99% ethanol, followed by bleach and again in ethanol after which the roots were held in a flame to burn off any ethanol remaining. The roots were then cut aseptically to expose microorganisms inside the plant. The exposed microorganisms were plated on agar medium selective for *Actinobacteria*. This was a low nutrient medium (mineral salts with a small amount of glucose). The plates were incubated at 28° C. for up to 6 weeks. When visible colonies had formed the cultures were isolated by several passes of single colony transfer onto fresh agar plates. Pure cultures were maintained on half-strength potato dextrose agar plates at room temperature. Spores from each pure culture were stored in water suspensions at room temperature or in 20% glycerol at −20° C. and/or −80° C. The isolates were maintained by inoculating the spore suspension onto fresh half-strength potato dextrose agar plates approximately 6 monthly or as needed.

The isolates were designated MH71 and MH243 and were deposited with the National Measurement Institute (NMI), Australia. MH71 was deposited on 21 Feb. 2017 under Accession Number V17/004100, and MH243 was deposited on 21 Feb. 2017 under Accession Number V17/004101.

Figure 10:
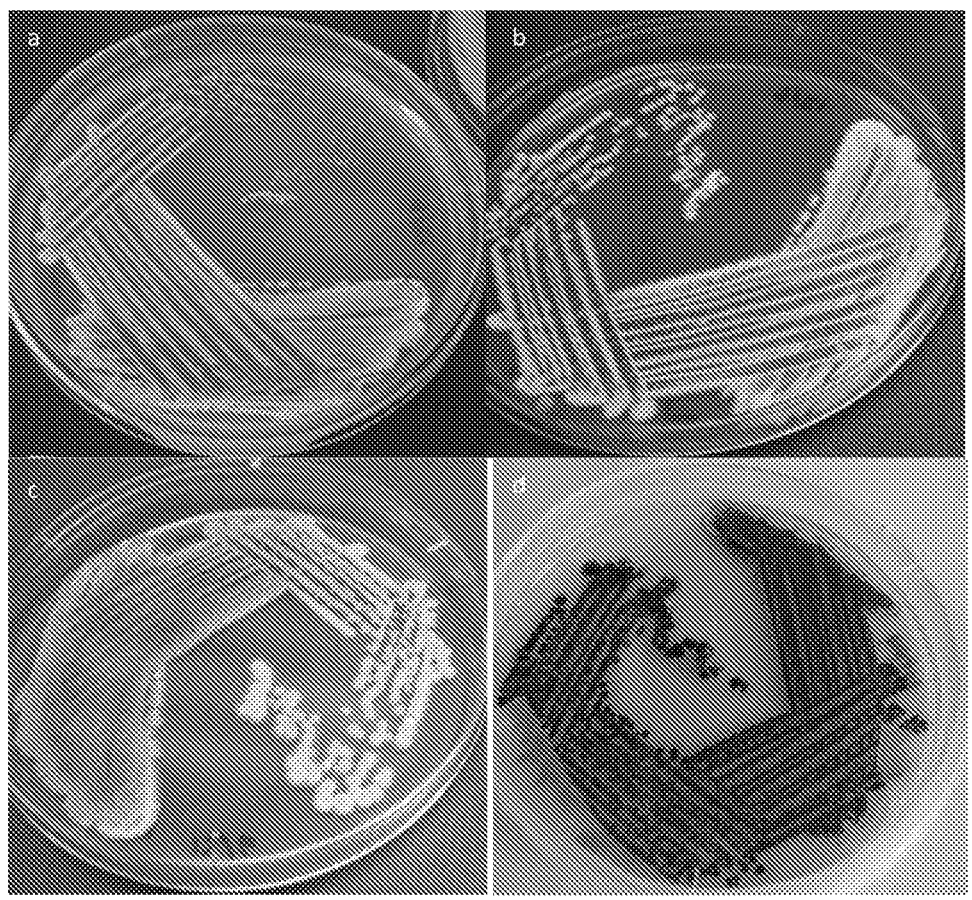
FIG. 10. Shows MH71 morphology on half strength potato-dextrose agar after 4 days (a), 7 days (b), 14 days (c) and 5 weeks (d).
Figure 11:
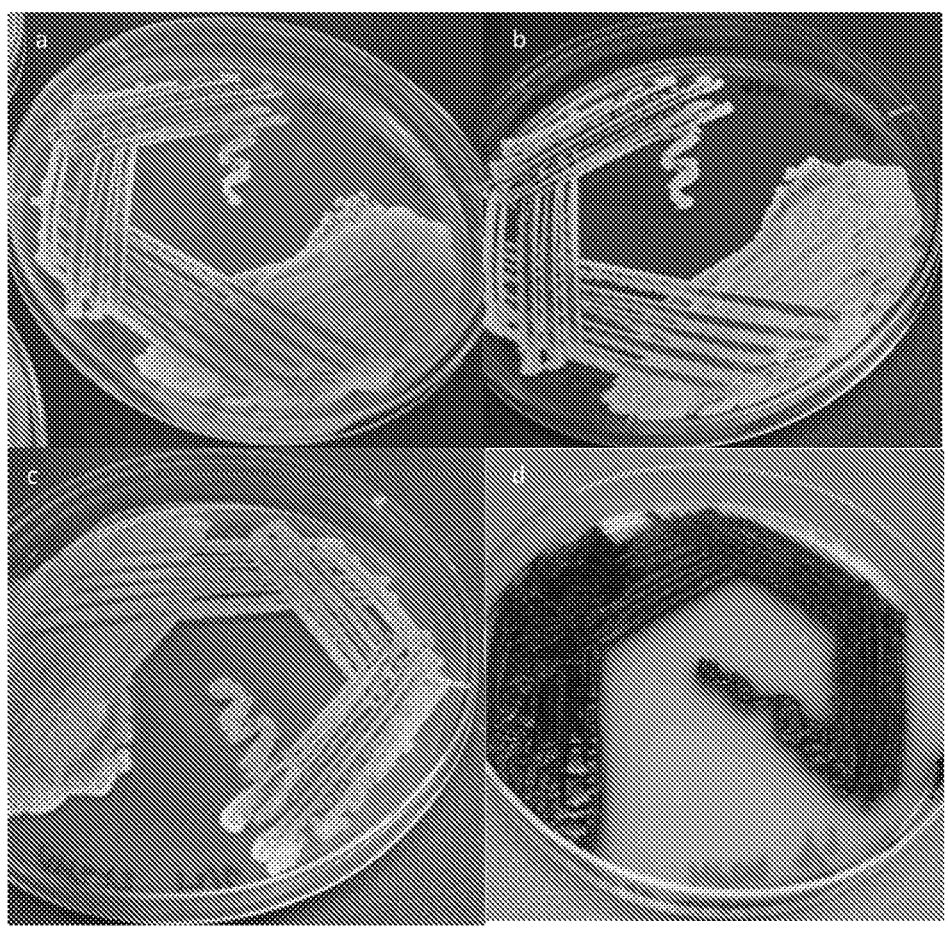
FIG. 11. Shows MH243 morphology on half strength potato-dextrose agar after 4 days (a), 7 days (b), 14 days (c) and 5 weeks (d).

MH71 and MH243 typically have the following morphological characteristics. When cultured on half-strength potato-dextrose-agar plates the two cultures are similar in appearance but their morphologies vary throughout their life cycle. Round, matt, raised, opaque, cream colonies that dig into the agar surface appear 3 to 5 days after plate inoculation. At these early growth stages the colonies are solid and hard and very resistant to removal with an inoculation loop. As the colonies age they begin to turn grey. After 3 weeks of growth the colonies develop a glossy black color and soften to very malleable texture. During this stage the colonies begin to form spores. Later a white, fringe (of spores) appears on the outer boundary of the colony (see FIGS. 10 and 11).

When grown in yeast malt extract (YME) broth both cultures are very similar in appearance. After approximately 1 week flocks of biomass appear floating throughout the broth. After several more days distinct circular white colonies appear floating at the air-water interface, particularly around the edges of the growth vessel where the water meets the glass or plastic. When viewed closely, these colonies are similar in appearance to mature colonies on plates (grey in the center and matte white around the edges.)

The isolates were assessed for their ability to suppress individual pathogens both in agar culture and small plant assays.

Antifungal metabolite production—Agar plate assays—Agar plate assays to test for suppression of pathogenic fungi by isolates were conducted by co-inoculating the test organism and the fungal pathogen at opposite ends of a potato-dextrose agar plate. A second plate was inoculated at one end with the fungal pathogen alone as a control. The plates were incubated at 28° C. in the dark until the control plate was completely covered by the pathogen. The level of inhibition of the fungal pathogen by the isolates was measured as the distance between the growing front of the test organism and the fungus on the day that the fungus had completely covered the control plate.

Small plant assays—the effectiveness of several of the *Actinobacteria*, including MH71 and MH243 has been tested in small plant assays for control of root diseases caused by the pathogens *Fusarium pseudogramininarum* (crown rot), *Pythium* spp. (*pythium* damping off), *Rhizoctonia solanii* (bare patch) and *Gaeumannomyces graminis* (Take all). Small plant tests have also been completed to test effectiveness in controlling foliar diseases *Sclerotinia sclerotiorum* on canola and powdery mildew on wheat.

For the small plant assays of root diseases, surface sterilised wheat (*Triticum aestivum*) seeds were coated with spores of test organisms. Seeds were then wrapped in a wet paper towel (Yang X, Ma J, Li H, Ma H, Yao J, Liu C (2010). 'Different genes can be responsible for crown rot resistance at different development stages of wheat and barley'. European Journal of Plant Pathology v128, 495-502) which was placed in a beaker and kept moist. Once the wheat plants protruded from the top of the paper rolls, 2 ml of a $10^6$/ml spore suspension of the test pathogen was introduced. After 2 weeks, plants were scored for disease severity and root and shoot length.

For small plant assays of *Sclerotinia sclerotiorum*, canola was planted in 15 cm diameter pots. When the seedlings were established they were sprayed with an aqueous solution of the test *Actinobacteria*, including MH71 and MH243. Twenty-four hours later they were inoculated with a 10 uL droplet of *Sclerotinia sclerotiorum* mycelial suspension. Disease severity was scored 4 days later.

Example 2

Direct Suppression of Fungal Pathogens by *Actinobacteria* Isolates

Antifungal Metabolite Production—In Vitro Assays

In vitro (agar plate) assays were used as an initial screen to assess the suppression of fungal pathogen growth due to bioactive compound production (e.g. metabolites) by the *Actinobacteria* isolates. Agar plate inhibition assays were conducted by co-inoculating the test organism (*Actinobacteria*) and the fungal pathogen at opposite ends of a nutrient agar plate. A second plate was inoculated at one end with the fungal pathogen alone as a control. The plates were incubated at 28° C. in the dark until the control plate was completely covered by the pathogen. The level of inhibition of the fungal pathogen by the *Actinobacteria* was measured as the distance between the growing front of the test organism and the fungus on the day that the fungus had completely covered the control plate (examples shown in FIG. 1). Percentage inhibition was then calculated relative to the distance between the test fungus inoculation point and the test *Actinobacteria* growing edge.

Figure 2:
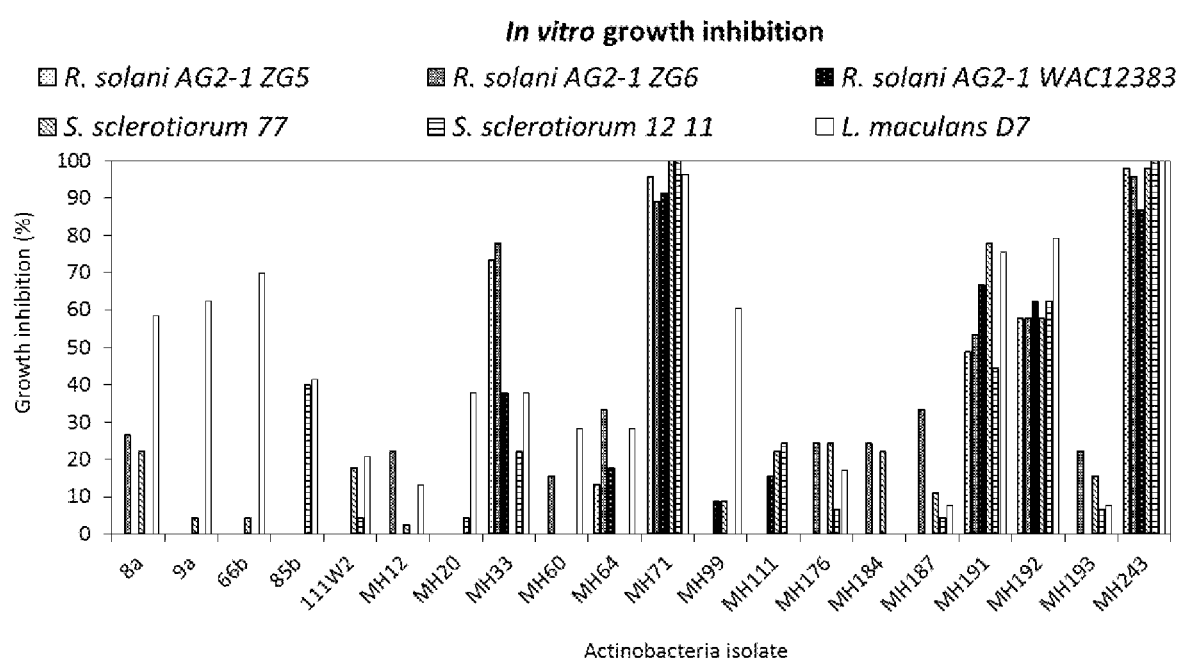
FIG. 2. Shows the results of in vitro suppression (shown as percentage inhibition) of fungal pathogens of canola by 20 different isolates of Actinobacteria. Note that isolates MH71 and MH243 had the highest levels of suppression against all pathogens tested when screened against isolates from the CSIRO Actinobacteria culture collection.
Figure 7:
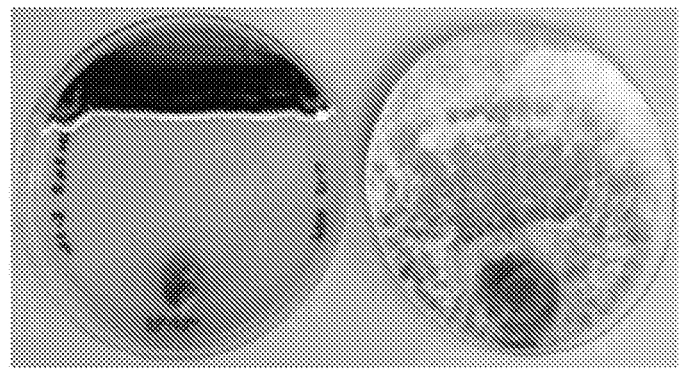
FIG. 7. Shows the results of in vitro antifungal activity of Actinobacteria against three F. pseudograrninearum strains.
Figure 8:
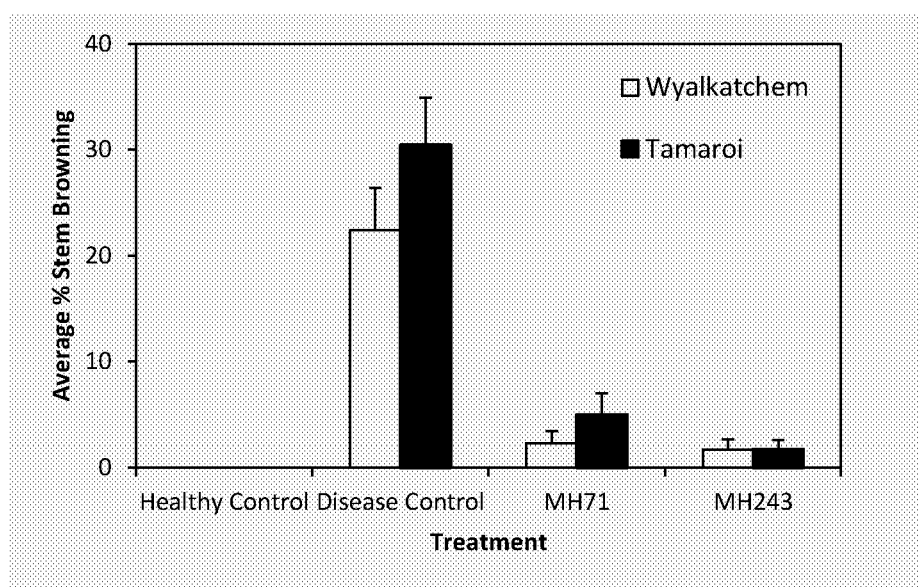
FIG. 8. Presents the results of an analysis showing consistent response of Fusarium pseudograrninearum inhibition by MH71 and MH243 across 2 wheat cultivars with differing disease susceptibility. For each treatment the left hand bars represent the wheat cultivar Wyalkatchem, and the right hand bars represent the wheat cultivar Tamaroi.
Figure 9:
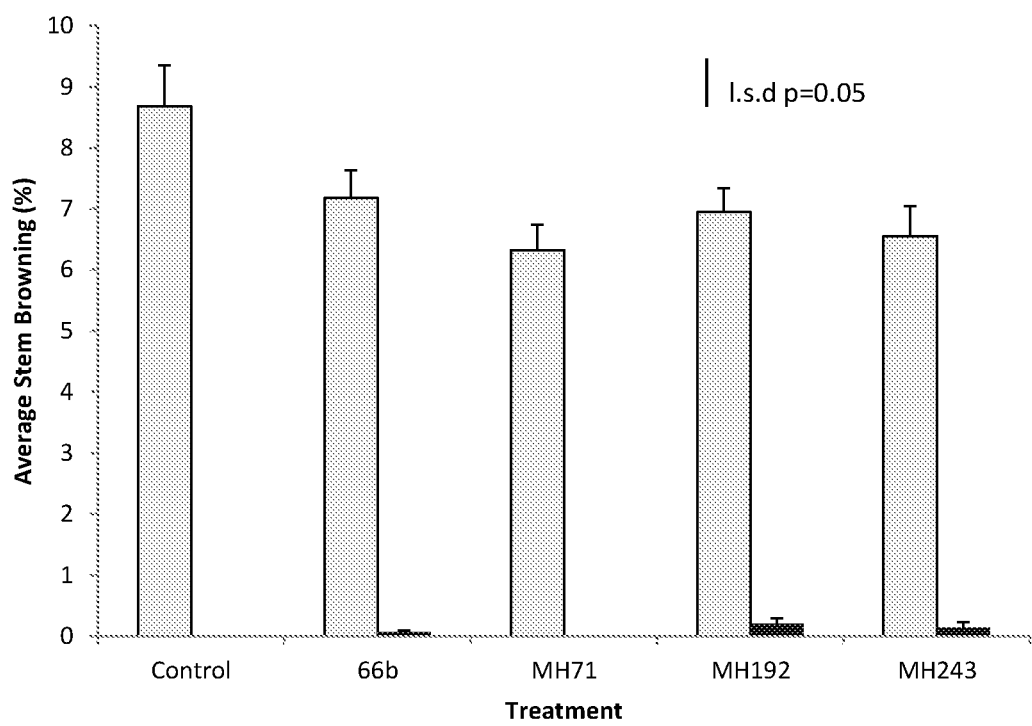
FIG. 9. Shows the results of glasshouse trials of wheat plants grown to maturity and demonstrates that MH71 and MH243 reduced disease by 27% and 25% respectively. Grey bars represent diseased plants; black bars represent healthy plants.
Figure 12:
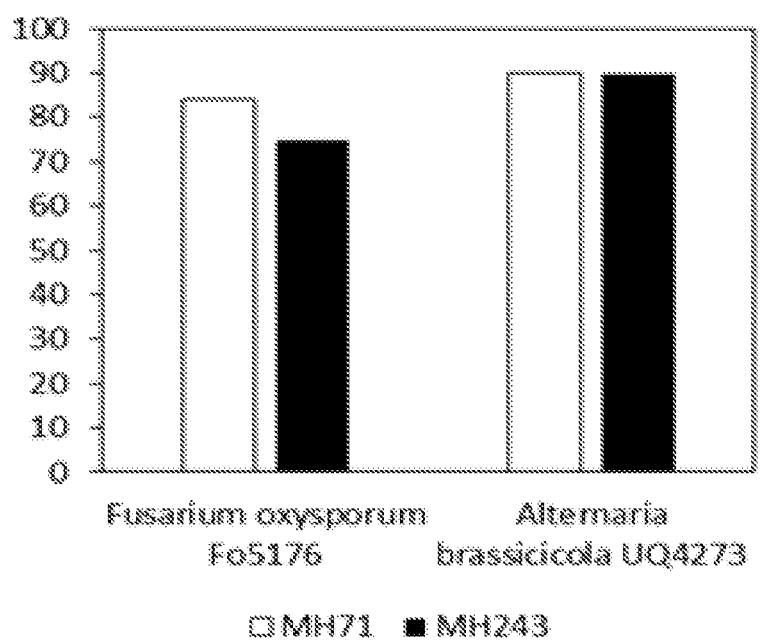
FIG. 12. Shows the results of suppression of Fusarium oxysporum and Alternaria brassicicola by MH71 and MH243 in vitro suppression assays. Isolates MH71 and MH243 were consistently effective in suppressing fungal growth by 90% for Alternaria brassicicola and 74-85%, respectively, for Fusarium oxysporum.

In in vitro assays, metabolites produced by *Actinobacteria* isolates and presumed secreted into the agar medium inhibited the growth of wheat pathogens *Fusarium pseudograminearum* (FIG. 7) by 78-100%, *Pythium irregulare* by up to 49% and *Gaeumannomyces graminis* (Take-all) by 13-82%. Activity against the *brassica* pathogens *Fusarium oxysporum* Fo5176 and *Alternaria brassicicola* was also assessed. Inhibition of these pathogens by 74-85% and 90%, respectively, was demonstrated (FIG. 12). For canola pathogens, the isolates MH71 and MH243 inhibited the growth of *Sclerotinia sclerotiorum* by 98-100%, of *Rhizoctonia solani* AG2-1 by 87-98%, and *Leptosphaeria maculans* by 96-100% (FIG. 2). Overall, for both wheat and canola, isolates MH71 and MH243 were most effective in suppressing pathogen growth. These *Actinobacteria* isolates were further assessed for their ability to suppress diseases in wheat and canola plants (in vivo).

Example 3

Biocontrol of Diseases in Wheat Plants

*Rhizoctonia* and *Pythium*

Figure 3:
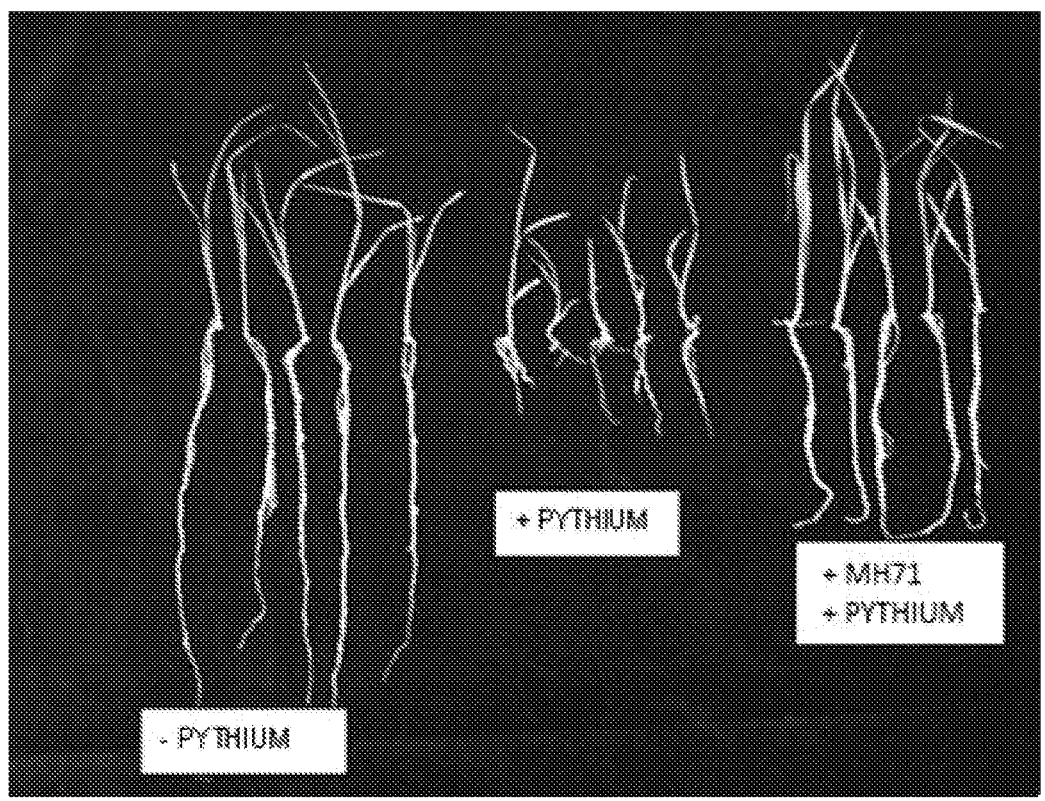
FIG. 3. Shows that inoculation with selected Actinobacteria significantly increased biomass of wheat plants infected with Pythium irregulare.

Initially glasshouse experiments with each of these diseases focused on plant growth in 4-week old wheat plants inoculated with and without the disease in question in the presence or absence of the test *Actinobacteria* isolate (applied as a seed coat with xanthan gum for treating root diseases). Differences in plant biomass were recorded as a measure of disease protection. Compared with disease-only controls, isolate MH71 increased plant biomass in the presence *Rhizoctonia* or *Pythium* (e.g. FIG. 3).

*Fusarium* Crown Rot

Figure 4:
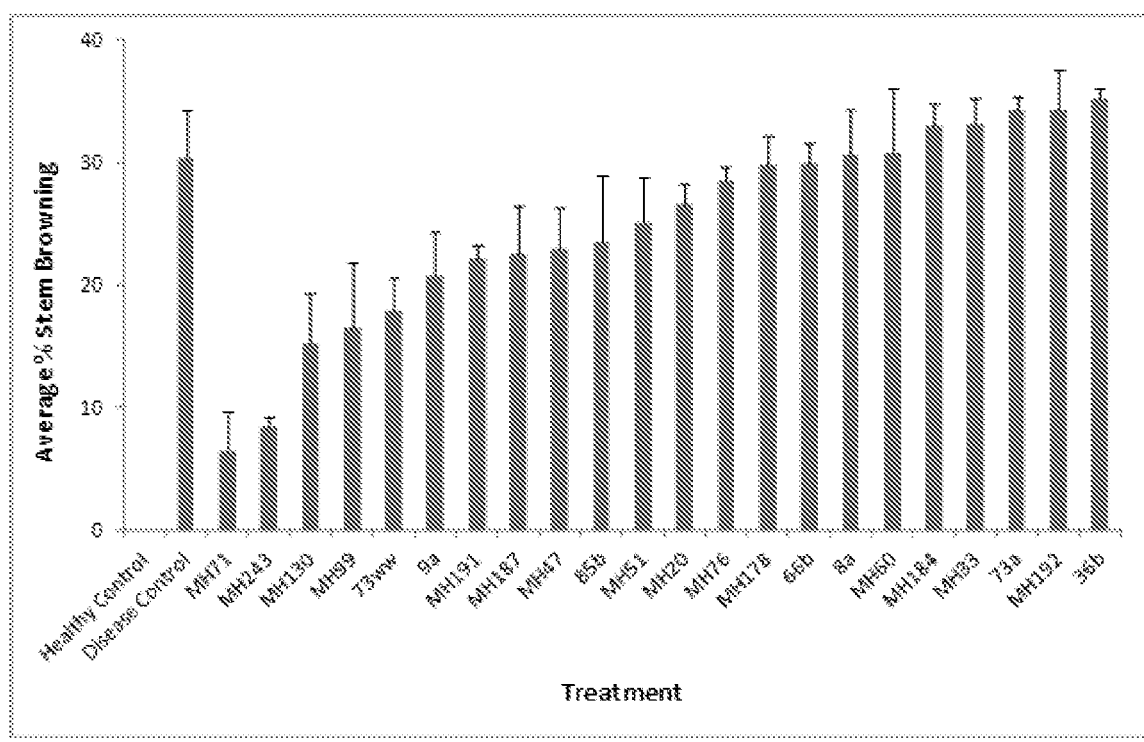
FIG. 4. Shows the results of suppression of Fusarium crown rot by Actinobacteria isolates in small plant assays. Isolates MH71 and MH243 were consistently effective in suppressing disease in multiple assays by between 75 and 94%.

In small plant assays (soil free), surface sterilised wheat (*Triticum aestivum*) seeds were coated with spores of test *Actinobacteria*. Seeds were then wrapped in a wet paper towel which was placed in a beaker and kept moist. Once the wheat plants protruded from the top of the paper rolls, 2 ml of a $10^6$/ml spore suspension of the test pathogen was introduced. Plants were scored for disease severity and root and shoot length after 2 weeks (FIG. 4) and crown rot disease was suppressed by between 75 and 94% by MH71 and MH243. In a glasshouse pot trial where wheat plants were grown to maturity, MH71 and MH243 suppressed crown rot severity by 27% and 25% respectively.

Example 4

Biocontrol of Diseases in Canola Plants

Figure 5:
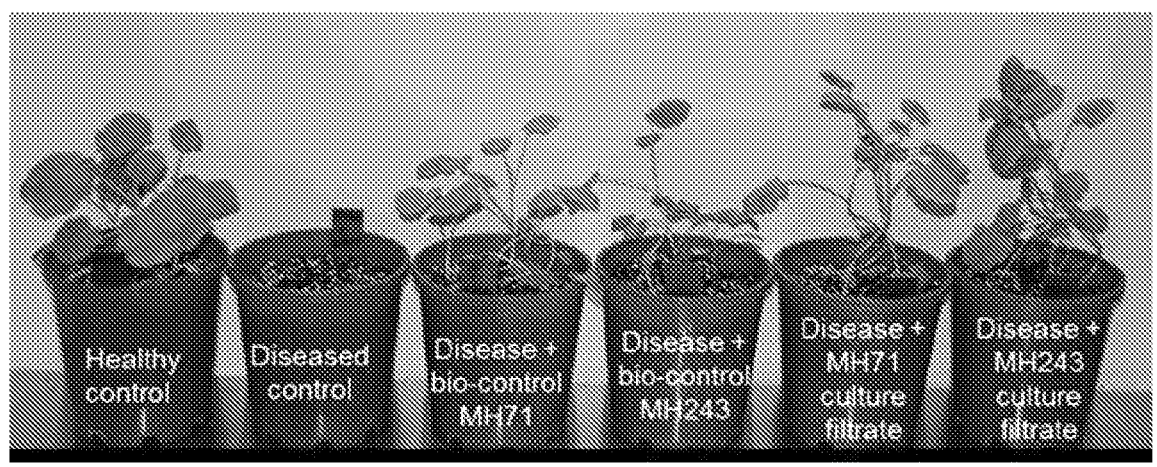
FIG. 5. Shows the results of in vivo suppression of Sclerotinia on canola by Actinobacteria. 10 day old canola seedlings were sprayed either with an Actinobacteria suspension (biocontrol), Actinobacteria cell free suspension (culture filtrate containing bioactives secreted into the broth medium), or no treatment. After 24 h a Sclerotinia mycelial suspension was applied to both cotyledons in disease treated plants. At 20 days post pathogen inoculation, plants inoculated with Actinobacteria survived and thrived. 'Disease only' treated seedlings died within 5-7 days.

In in vivo assays the *Actinobacteria* microorganisms applied as a foliar spray inhibited disease symptom development of the canola pathogen *Sclerotinia sclerotiorum* by 100%, with 100% plant survival compared with 0% survival in the 'disease only' control plants (FIG. 5). When tested against *Rhizoctonia solani* AG-2, the *Actinobacteria* isolates, applied as a seed coat, resulted in a 2-3-fold increase in survival compared with control (disease only) canola plants.

Example 5

Fungal Disease Suppression by Cell-Free Culture Filtrates

Figure 6:
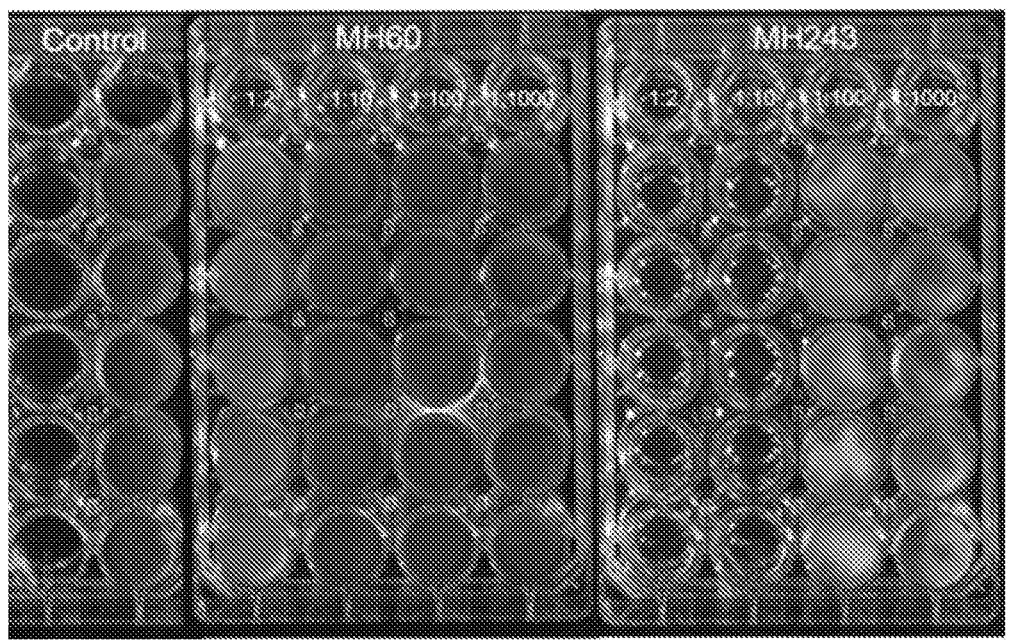
FIG. 6. Shows the results of in vitro suppression of Fusarium pseudograrninearum (A) and Sclerotinia sclerotiorum (B) by Actinobacteria culture filtrates. A dilution series of isolate MH243 culture filtrate (cell free) suppressed the growth of F. pseudograrninearum (up to 1/100 dilution and S. sclerotiorum mycelia (up to 1/1000 dilution). MH60 is shown as a representative non-suppressor Actinobacteria isolate.
Figure 6:
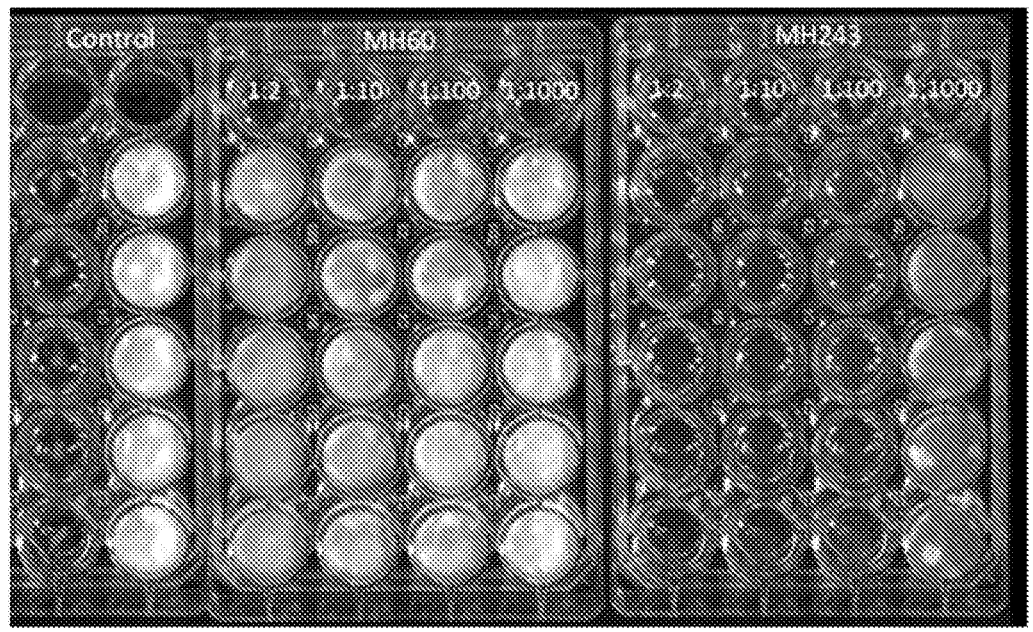

Compounds secreted by the isolates MH71 and MH243 (in the form of a culture filtrate) exhibit high biofungicide efficacy demonstrated in in vitro assays against both *F. pseudograrninearum* and *S. sclerotiorum* (FIG. 6), and in in vivo assays against the pathogen *S. sclerotiorum* on canola (FIG. 5).

The isolates were grown separately as pure cultures in sterile Yeast Malt Extract (YME) broth for a minimum of 4 weeks at room temperature (at approx. 25° C.) with no shaking. For cell free filtrates, the broths were course filtered through miracloth and then passed through 0.22 micron Milli-pore syringe filters.

In in vitro assays the *Actinobacteria* culture filtrate (cell free) of MH71 and MH243 prevented fungal growth of the wheat pathogen *F. pseudograrninearum* at dilutions up to 1 in 10 and the canola pathogen *S. sclerotiorum* at dilutions up to 1 in 100. Fungal growth of *F. pseudograrninearum* and *S. sclerotiorum* were severely inhibited at dilutions of 1/100 and 1/1000 respectively.

In in vivo (seedling) assays, the *Actinobacteria* culture filtrate (cell free) of MH71 and MH243 inhibited disease symptom development of the canola pathogen *S. sclerotiorum* by 100% with survival rates 100% above 'disease only' control plants.

Example 6

Mature Plant Pot Study

Figure 13:
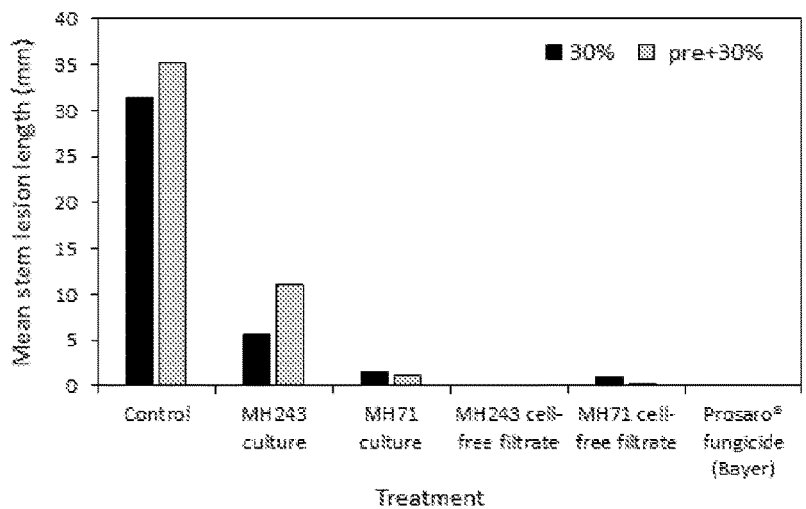
FIG. 13. Shows the results of mature canola plant pot studies using Actinobacteria microbe or cell-free filtrate treatment of plants inoculated with Sclerotinia as compared to control inoculated plants and plants treated with the commercial fungicide for Sclerotinia control (Prosaro, Bayer). Plants were sprayed at 30% bloom, or 10 and 30% bloom (flowering) stage.
Figure 13:
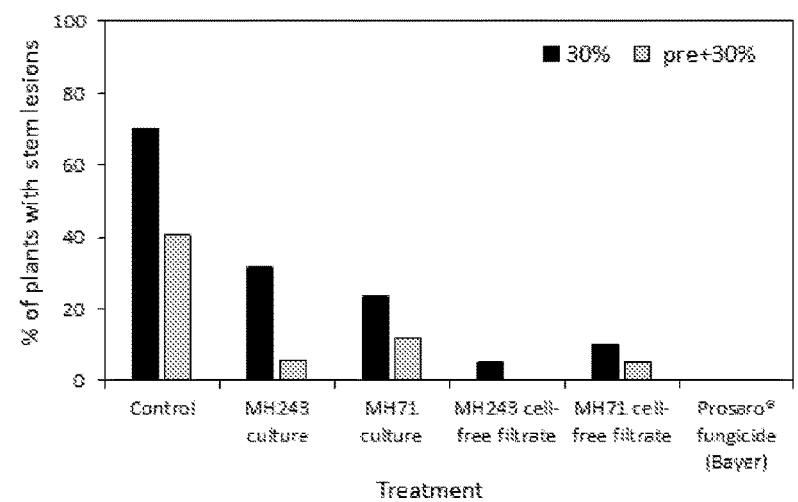
Figure 13:
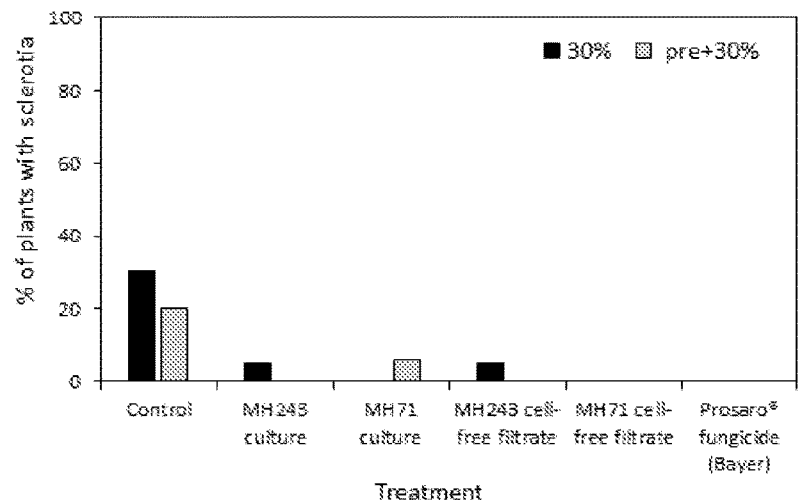

Mature canola plants were sprayed at 30% bloom, or received two sprays (one at pre-flowering (~10% bloom stage) and the second at 30% bloom). Plants were sprayed with either *Actinobacteria* or cell free filtrate (FIG. 13).

Included were control treated plants and plants treated with a commercial fungicide used for *Sclerotinia* control (Prosaro, Bayer). Results were recorded at 21 days post *Sclerotinia* inoculation. The *Actinobacteria* microbe or cell-free filtrate treatments also positively influenced final grain yield and grain weight compared to control treated plants.

Example 7

Whole Genome Sequencing and Identification

PCR-based 16s ribosomal DNA sequencing of MH71 and MH243 was unable to provide an identification to the species level. The 16s sequencing confirmed that both MH71 and MH243 belong to the *Streptomyces* genus. Full genome sequencing was conducted and confirmed both MH71 and MH243 are *Streptomyces* spp. Best BlastN hits from analysis of several housekeeping genes (atpD, gyrB, recA, rpoB and trpB) suggests MH71 and MH243 belong to the *Streptomyces hygroscopicus* Glade. Further, whole genome blast2go analysis revealed the closest neighbour for both MH71 and MH243 is identified as *Streptomyces violaceusniger*.

Example 8

Bacterial Pathogen Suppression by Cell-Free Culture Filtrates

Figure 14:
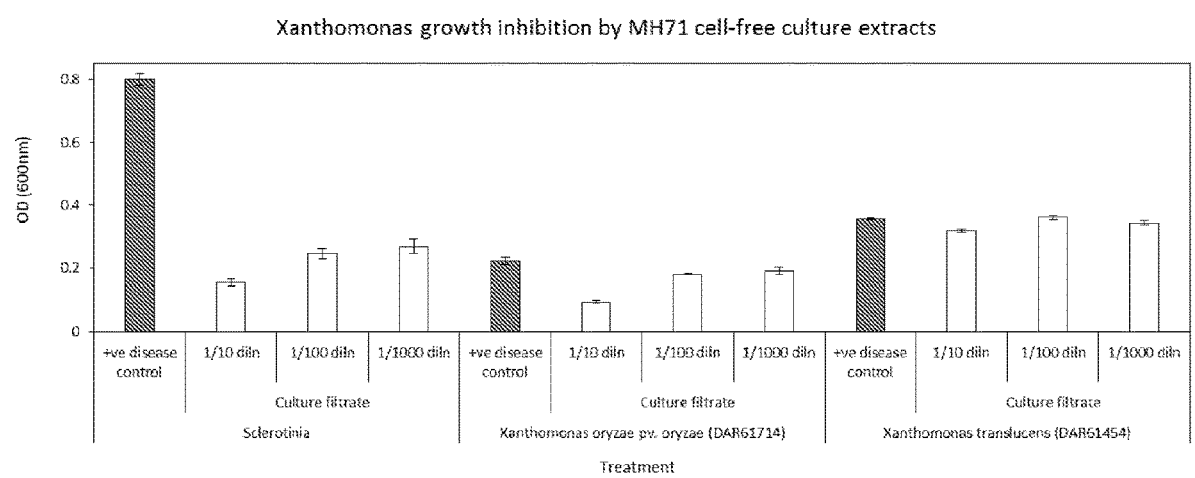
FIG. 14. Shows the results of in vitro suppression (shown as a decrease in optical density (OD)) of bacterial pathogens of rice (Xanthomonas) by cell-free extracts from MH71. Inhibition of a representative fungal pathogen, Sclerotinia, is provided as comparison of bio-bactericide efficacy against bio-fungicide efficacy.

Compounds secreted by the isolate MH71 (in the form of a culture filtrate) exhibit bio-bactericide efficacy demonstrated in in vitro assays against *Xanthomonas* species, against *Xanthomonas* species, *Xanthomonas translucens* (DAR61454) responsible for bacterial leaf streak/black chaff disease on wheat, and *Xanthomonas oryzae* pv. *oryzae* (DAR61714) responsible for bacterial blight disease on members of the *Oryza* genus including rice (*Oryza sativa*) (FIG. 14). Compounds secreted by isolates MH71 and MH243 (in the form of a culture filtrate) exhibit high bio-bactericide efficacy demonstrated in in vitro assays against *Pseudomonas* species, *Pseudomonas syringae* (BRIP47231 and BRIP34869) responsible for rot disease on members of the *Hordeum* genus including barley (*Hordeum vulgare*) (FIG. 15).

The MH71 and MH243 isolates were grown as pure cultures in sterile Yeast Malt Extract (YME) broth for a minimum of 4 weeks at room temperature (at approx. 25° C.) with no shaking. For cell free filtrates, the broth was course filtered through miracloth and then passed through 0.22 micron Milli-pore syringe filter.

As shown in FIG. 14, in in vitro assays culture filtrate (cell free) of MH71 prevented bacterial growth of the *Oryza* pathogen *Xanthomonas oryzae* pv. *oryzae* (DAR61714) at a dilution of 1 in 10.

Figure 15:
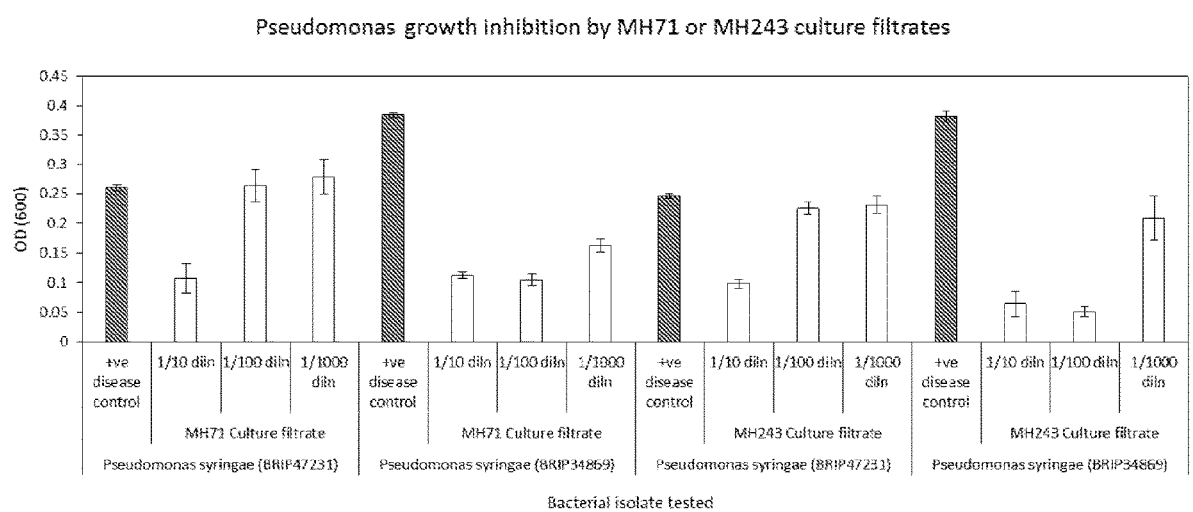
FIG. 15. Shows the results of in vitro suppression (shown as a decrease in optical density (OD)) of bacterial pathogens of barley (Pseudomonas) by cell-free extracts from MH71 and MH243. Inhibition of a representative fungal pathogen, Sclerotinia, is provided as comparison of bio-bactericide efficacy against bio-fungicide efficacy.

As shown in FIG. 15, in in vitro assays culture filtrates (cell free) of MH71 and MH243 prevented bacterial growth of the barley pathogens *Pseudomonas syringae* BRIP47231 and BRIP34869 at dilutions of 1 in 10. Bacterial growth of *Pseudomonas syringae* BRIP34869 was severely inhibited at dilutions of 1 in 100 by both MH71 and MH243 filtrates.

In in vitro assays, metabolites produced by isolate MH71 and presumed secreted into the culture filtrate (cell free) medium inhibited the growth of *Oryza* pathogen *Xanthomonas oryzae* pv. *oryzae* (DAR61714) up to 58%, and of barley pathogens *Pseudomonas syringae* (BRIP47231) up to 59% and *Pseudomonas syringae* (BRIP34869) up to 71% when diluted 1 in 10 (FIGS. 14 and 15).

In in vitro assays, metabolites produced by isolate MH243 and presumed secreted into the culture filtrate (cell free) medium inhibited the growth of barley pathogens *Pseudomonas syringae* (BRIP47231) by up to 60% and *Pseudomonas syringae* (BRIP34869) up to 83% when diluted 1 in 10 (FIG. 15).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method for treating an infection of a plant by a fungal or bacterial pathogen or a disease of a plant caused by or associated with infection by the pathogen, comprising applying *Streptomyces* isolate MH71 deposited with the National Measurement Institute, Australia, under deposit number V17/004100 and/or *Streptomyces* isolate MH243 deposited with the National Measurement Institute, Australia, under deposit number V17/004101 to the plant, a plant part or plant surrounds, wherein the pathogen is selected from a species of *Leptosphaeria, Alternaria, Xanthomonas, Pseudomonas,* or *Fusarium oxysporum*.

2. A method according to claim 1, wherein the infection is not *Fusarium* crown rot.

3. A method according to claim 1, wherein the pathogen is a fungal pathogen.

4. A method according to claim 3, wherein the fungal pathogen is selected from *Fusarium oxysporum, Leptosphaeria maculans,* and *Alternaria brassicicola*.

5. A method according to claim 1, wherein the pathogen is a bacterial pathogen.

6. A method according to claim 5, wherein the bacterial pathogen is *Xanthomonas oryzae* pv. *oryzae*, or *Pseudomonas syringae*.

7. A method according to claim 1, wherein the plant is a crop plant.

8. A method according to claim 7, wherein the crop plant is canola, wheat, soybean or rice.

* * * * *